United States Patent [19]

Tarcsay et al.

[11] 4,406,890

[45] Sep. 27, 1983

[54] NOVEL LIPOPHILIC MURAMYL PEPTIDES AND PROCESSES FOR THEIR MANUFACTURE

[75] Inventors: Lajos Tarcsay, Grenzach-Wyhlen, Fed. Rep. of Germany; Gerhard Baschang, Bettingen, Switzerland; Albert Hartmann, Grenzach, Fed. Rep. of Germany; Jaroslav Stanek, Birsfelden, Switzerland

[73] Assignee: Ciba-Geigy Corporation, Ardsley, N.Y.

[21] Appl. No.: 283,759

[22] Filed: Jul. 16, 1981

Related U.S. Application Data

[63] Continuation-in-part of Ser. No. 172,035, Jul. 24, 1980, abandoned, and a continuation-in-part of Ser. No. 226,966, Jan. 21, 1981.

[30] Foreign Application Priority Data

Jul. 25, 1979 [CH] Switzerland .......................... 6893/79

[51] Int. Cl.$^3$ .................... A61K 37/02; C07C 103/52; C07G 7/00
[52] U.S. Cl. ............................. 424/177; 260/112.5 R; 424/85
[58] Field of Search .................... 260/112.5 R; 424/85, 424/177

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,101,536 | 7/1978 | Yamamura et al. | 260/112.5 R |
| 4,185,089 | 1/1980 | Derrien et al. | 260/112.5 R |
| 4,235,771 | 11/1980 | Adam et al. | 260/112.5 R |

OTHER PUBLICATIONS

Annual Reports in Medicinal Chemistry-14, Chapter 15, Immunostimulants, pp. 147-161, 1979.

Primary Examiner—Blondel Hazel
Attorney, Agent, or Firm—Irving N. Feit

[57] ABSTRACT

The invention relates to muramyl peptide compounds, especially of the formula $$\begin{array}{c} CH_2OH \\ \diagdown O \\ HO \diagup \diagdown OH,H \\ \diagup N-X-R_1 \\ R_3-CH \quad R_2 \\ \diagdown \quad R_5 \quad COA_1 \quad R_7 \\ CON-CH-CON-CH-CH_2CH-COA_2 \\ R_4 \quad R_6 \\ (D) \quad (L) \quad (D) \end{array} \quad (I)$$

in which
$R_1$ represents, for example, alkyl or phenyl,
$R_3$ represents, for example, hydrogen or methyl and
$R_5$ represents, for example, hydrogen or lower alkyl optionally substituted, for example, by hydroxy, mercapto, or methylthio, and in which one of the radicals
$A_1$ and $A_2$ represents a group of the formula $$\begin{array}{c} O \quad W \\ \| \quad | \\ T-Y-O-P-O-CH \\ | \quad | \\ OH \quad Z \end{array}$$

in which
T represents the group of the formula -NH or -O, and
Y represents an alkylene radical optionally interrupted by a radical of the formula -CO-O- or -CO-NH-,
and in which
W represents hydrogen and
Z represents a hydroxy-substituted ethyl group, wherein at least one hydroxy group is esterified by a long-chained acyl radical or
W and Z represent hydroxymethyl, wherein hydroxy is esterified by a long-chained acyl radical, and the other of the radicals $A_1$ and $A_2$ represents optionally etherified hydroxy or optionally substituted amino.

The novel compounds have immunopotentiating properties.

43 Claims, No Drawings

NOVEL LIPOPHILIC MURAMYL PEPTIDES AND PROCESSES FOR THEIR MANUFACTURE

This is a continuation-in-part application of U.S. applications Ser. No. 172,035, filed July 24, 1980 now abandoned, and Ser. No. 226,966, filed Jan. 21, 1981.

The invention relates to novel lipophilic muramyl peptides, also to processes for their manufacture and to pharmaceutical preparations that contain these lipophilic muramyl peptides, and also to their use for stimulating immunity.

The invention relates especially to compounds of the formula

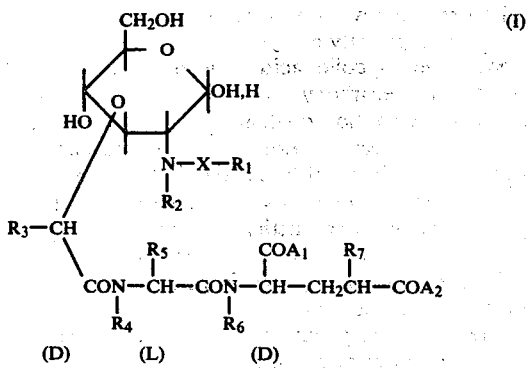

in which

X represents carbonyl or carbonyloxy, $R_1$ represents optionally substituted alkyl or aryl, $R_2$, $R_4$ and $R_6$ represent hydrogen or lower alkyl, $R_3$ represents hydrogen or lower alkyl, $R_5$ represents hydrogen, lower alkyl, free or functionally modified hydroxy-lower alkyl, free or functionally modified mercapto-lower alkyl, optionally substituted amino-lower alkyl, cycloalkyl, cycloalkyl-lower alkyl, optionally substituted aryl or aralkyl, or nitrogen-containing heterocyclyl or heterocyclyl-lower alkyl, or $R_4$ and $R_5$ together also represent alkylene having 3 or 4 carbon atoms, $R_7$ represents hydrogen or optionally esterified or amidated carboxyl and one of the radicals $A_1$ and $A_2$ represents a radical of the formula

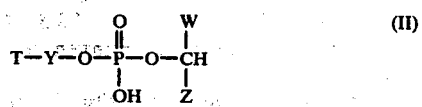

in which

T represents -NH or -O,

Y represents an optionally substituted alkylene group which may also be interrupted by one or two oxycarbonyl and/or iminocarbonyl groups, W represents hydrogen, and Z represents a 1,2-dihydroxyethyl or 2-hydroxyethyl group in which at least one of the hydroxy groups is esterified by an optionally unsaturated, long-chained aliphatic carboxylic acid or etherified by an optionally unsaturated, long-chained aliphatic alcohol, or W and Z each represents a hydroxymethyl group esterified by an optionally unsaturated, long-chained aliphatic carboxylic acid or etherified by an optionally unsaturated, long-chained aliphatic alcohol, and the other of the radicals $A_1$ and $A_2$ represents free or etherified hydroxy, amino, lower alkylamino or aminocarbonyl-lower alkylamino and to salts thereof.

Alkyl is especially straight-chain or branched alkyl bonded in any position and having up to 18 carbon atoms, especially lower alkyl.

Substituents of the optionally substituted alkyl groups are especially free or functionally modified hydroxy or mercapto groups, such as etherified or esterified hydroxy or mercapto groups, for example lower alkoxy or lower alkylthio groups, or halogen atoms, or free or functionally modified carboxyl groups, such as lower alkoxycarbonyl or carbamoyl groups. The substituted alkyl radical, such as the lower alkyl radical may carry one, two or more identical or different substituents, especially free hydroxyl groups or halogen atoms.

Aryl radicals are especially monocyclic and also bicyclic aryl radicals, especially phenyl, and also naphthyl. They may optionally be mono-, di- or polysubstituted, for example by lower alkyl groups, by free, esterified or etherified hydroxy, for example lower alkoxy or lower alkylenedioxy, or by halogen atoms, and/or by trifluoromethyl groups.

Aralkyl is especially aryl-lower alkyl, in which aryl has the meaning given above. Aryl-lower alkyl is especially benzyl or phenylethyl, in which the phenyl nucleus may be mono-, di- or poly-substituted.

Optionally substituted aralkyl radicals are especially those radicals that, in the aromatic nucleus, are optionally mono-, di- or poly-substituted, for example by lower alkyl, free, etherified or esterified hydroxy or mercapto groups, for example lower alkoxy or lower alkylenedioxy, and also by lower alkylthio or trifluoromethyl groups and/or by halogen atoms.

Cycloalkyl is especially cycloalkyl having 5 or 6 carbon atoms, such as cyclopentyl or cyclohexyl, and cycloalkyl-lower alkyl is especially one in which the cycloalkyl radical has 5 or 6 carbon atoms and the lower alkyl radical is especially methyl or ethyl.

Nitrogen-containing heterocyclyl is especially the radical of a 5- or 6-membered heterocyclic compound containing one or two nitrogen atoms in the ring. It may be unsaturated or saturated, and contain, for example, a condensed phenyl radical. Pyrrolyl, indolyl, pyridyl or imidazolyl radicals may be mentioned as examples thereof.

In nitrogen-containing heterocyclyl-lower alkyl, the heterocyclyl radical has the meaning mentioned above and the lower alkyl radical is especially methyl or ethyl. 4-Imidazolylmethyl or 3-indolylmethyl may be mentioned as examples thereof.

The alkylene radical which may be formed by the radicals $R_4$ and $R_5$ is preferably unsubstituted and is especially the trimethylene radical.

An optionally esterified or amidated carboxyl group is especially the carboxyl group itself, or a carboxyl group esterified by a lower alkanol or also the carbamoyl group which, at the nitrogen atom, is unsubstituted or mono- or di-substituted by alkyl, especially lower alkyl, aryl, especially phenyl, or aralkyl, such as benzyl. Alternatively, the carbamoyl groups may also carry an alkylene radical, such as the tetra- or penta-methylene radical.

Optionally functionally modified hydroxy or mercapto groups are especially etherified or esterified hydroxy or mercapto groups such as lower alkoxy, lower acyloxy, for example lower alkanoyloxy, or halogen atoms, lower alkylthio or lower acylthio, for example lower alkanoylthio.

Functionally modified amino-lower alkyl is especially mono- or di-lower alkylamino-lower alkyl or acylated amino-lower alkyl, such as methylamino-, ethylamino-, dimethylamino-, diethylamino- and alkanoylamino-lower alkyl, for example lower alkanoylamino-lower alkyl.

Aminocarbonyl-lower alkylamino is especially 1-aminocarbonyl-lower alkylamino, for example aminocarbonylmethylamino, 1-aminocarbonyl-ethylamino, 1-aminocarbonylisobutylamino or 1-aminocarbonyl-3-methyl-butylamino.

The alkylene radical Y is especially a lower alkylene radical, preferably having 2 or 3 carbon atoms. The alkylene radical Y may, however, also be a lower alkylene radical interrupted by a radical such as oxycarbonyl or $N-R_8$-iminocarbonyl, and is then especially a radical of the formula

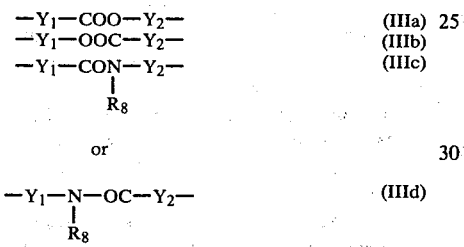

in which one of the radicals $Y_1$ and $Y_2$ represents an optionally substituted lower alkylene radical, and the other represents an optionally substituted lower alkylene radical which may also be interrupted by oxycarbonyl or $N-R_8$-iminocarbonyl, and $Y_1$ and $Y_2$ together have more than 2 carbon atoms, and $R_8$ represents hydrogen or lower alkyl. Substituents of the radicals $Y_1$ and $Y_2$ that should be given special mention are free or functionally modified hydroxy or hydroxy-lower alkyl, free or functionally modified mercapto or mercapto-lower alkyl, free or mono- or di-lower-alkylated or acylated amino-lower alkyl, aminocarbonyl, alkyl, cycloalkyl having 5 or 6 carbon atoms, aryl or aralkyl, wherein the general terms may have the meanings given above.

A long-chained aliphatic carboxylic acid is especially one having 12 to 90 carbon atoms, which may also have 1 or 2 double bonds and may be straight-chained or branched. Preferred are carboxylic acids having 16 to 22 carbon atoms, or natural or synthetic mycolic acids.

A long-chained aliphatic alcohol is especially an alkanol having 10 to 22 carbon atoms, which may also have one or two double bonds and may be straight-chained or branched. Preferred are those alkanols containing 12 to 18 carbon atoms, the hydroxy group of which is in the terminal position.

The radicals and compounds denoted by "lower" in the context of this description and the claims contain preferably up to and including 7, and especially up to and including 4, carbon atoms.

Hereinbefore and hereinafter the general terms may have the following meanings:

Lower alkyl is, for example, n-propyl, n-butyl, isobutyl, sec.-butyl or tert.-butyl, also n-pentyl, n-hexyl, isohexyl or n-heptyl and, especially, methyl or ethyl. In aryl-, cycloalkyl- or heterocyclyl-lower alkyl, the lower alkyl radical is especially methyl or ethyl, the aryl, cycloalkyl or heterocyclyl radical having the above-mentioned meaning.

Lower alkoxy is, for example, n-propoxy, n-butoxy, isobutoxy, sec.-butoxy or tert.-butoxy and, especially, methoxy or ethoxy.

Lower alkylthio is, for example, n-propyl-, n-butyl-, isobutyl-, sec.-butyl- or tert.-butylthio and, especially, methylthio or ethylthio.

Lower alkylenedioxy is especially methylenedioxy, ethylenedioxy or propylenedioxy.

Halogen represents fluorine or bromine, but preferably chlorine.

Lower alkanoyl is especially propionyl or butyryl, and more especially acetyl.

Synthetic mycolic acids are especially α-alkyl-β-hydroxyalkanecarboxylic acids, in which the alkyl radical in the α-position contains from 1 to 20, especially from 1 to 14, carbon atoms and the alkanecarboxylic acid contains from 20 to 80, especially from 30 to 34, carbon atoms. They may also contain further hydroxyl groups, and also oxo, methylene or ethylene groups.

Natural mycolic acids are especially those that may be isolated from living organisms, such as bacteria, for example mycobacteria.

The novel compounds of the present invention may exist in the form of mixtures of isomers or of pure isomers.

The radical of the formula $-CH(R_3)-C(=O)-$ linked to the oxygen atom, in the case where $R_3$ represents lower alkyl, is present in optically active form and has the D-form, whilst the radical of the amino acid of the formula $-N(R_4)-CH(R_5)-C(=O)-$, in the case when $R_5$ does not represent hydrogen, is likewise present in optically active form, namely in the L-form, and the terminal α-aminoglutaric acid radical is present in the D-form. Also, the optionally substituted 1-hydroxy group may have the α- or β-configuration; the novel compounds of the formula I may, however, alternatively be present in the form of a mixture of 1α- and 1β-isomers.

In the compounds of the formula I the proton bonded to phosphorus via an oxygen atom can readily be split off by bases. At a pH-value of 7 the compounds of the formula I are present mostly or totally in the form of the corresponding salts. For example, by the most comfortable (best) mode of purifying the compounds of the formula I (dialysis against a sodium phosphate buffer solution, pH 7) known to us the corresponding sodium salts are obtained. At a pH-value of 3.5 a 1:1-mixture of free acid and salt is present. The invention relates also to these salts.

The invention relates generally also to the salts of compounds of the formula I with any other salt-forming groups. Salt-forming groups that come into consideration are, for example, carboxyl groups that may be represented, for example, by the radicals $COA_1$, $COA_2$ or $R_7$, or amino groups in the radical $R_5$. The invention relates especially to pharmaceutically acceptable, non-toxic salts of the compounds of the formula I. Counter-ions of carboxylate anions to be given special mention are metal or ammonium ions, such as alkali metal and alkaline earth metal ions, for example sodium, potassium, magnesium or calcium ions, as well as ammonium ions from ammonia or suitable organic amines, such as lower alkylamines, for example triethylamine. The compounds of the formula I with basic groups, for example amino groups, can form acid addition salts. These compounds can e.g. be present in the form of inner salts, that is to say, zwitterions. The proton bonded to phosphorus by an oxygen atom can, for example, protonate an amino group in the radical $R_5$. For isolation or purification, pharmaceutically unacceptable salts may also be used. Only the pharmaceutically acceptable, non-toxic salts can be used therapeuctically, and are therefore preferred.

Only such salts or mixtures of salts with the free corresponding acids are stable in aqueous solution, which exhibit a pH-value between approximately 6 and 7.

The novel lipophilic muramyl peptides of the present invention and especially the pharmaceutically acceptable salts, e.g. sodium salts, thereof have a series of valuable pharmacological properties, especially a pronounced immunopotentiating action.

Thus, in vivo these compounds considerably increase the ability of mice to form antibodies:

NMRI mice are immunised by intraperitoneal injection of 10 μg of precipitate-free BSA on day 0. 9, 15 and 29 days later, serum samples are taken and examined for their content of anti-BSA antibodies using a passive haemagglutination technique. In the dose used, soluble BSA is sub-immunogenic for the recipient animals, that is to say, it is unable to initiate any, or only a very negligible, production of antibodies. Additional treatment of the mice with certain immunopotentiating substances before or after the administration of antigen leads to a rise in the antibody titre in the serum. The effect of the treatment is expressed by the score value achieved, that is to say, by the sum of $\log_2$ titre differences on the three days on which blood samples were taken.

In this test, on intraperitoneal or subcutaneous administration of from 0.5 to 5 mg/kg animal on five successive days after immunisation with BSA, the compounds of the formula (I) are able significantly to increase the antibody production against BSA. In this respect they are greatly superior to the conventional hydrophilic muramyl peptides.

Manifestations of the cell-imparted immunity can also be potentiated in vivo by the mentioned compounds:

Whereas sensitisation of guinea pigs with BSA in incomplete Freund's adjuvant results only in humoral formation of antibodies, the admixture of the lipophilic muramyl peptides according to the invention in a dose range of from 5 to 50 μg to the antigen-oil emulsion induces delayed hypersensitivity to BSA: three weeks after immunisation, intracutaneous injection of BSA in these animals results in a local inflammation with erythemia and thickening of the skin which reaches its maximum within 24 to 48 hours. These delayed reactions correspond quantitatively and qualitatively to those that are normally obtained by immunisation with BSA in complete Freund's adjuvant (that is, with the addition of mycobacteria). The $ED_{50}$ values (μg/animal required for the induction of a difference in the reaction volume of 200 μl, (erythemia area x increase in skin thickness) in treated and untreated animals 24 hours after induction) are from 10 to 20 μg.

Deserving of particular emphasis is also the ability of such lipophilic muramyl peptides, by administration together with BSA in liposomes (egg lecithin:cholesterol 4:1; 4 mg/animal) and without the toxic mineral oil component, to induce in guinea pigs a delayed hypersensitivity to BSA. Quantitatively and qualitatively these delayed reactions are likewise identical with those that are obtained by immunisation with BSA in complete Freund's adjuvant. The $ED_{50}$ values are 100 to 300 μg per animal.

Compared with hydrophilic muramyl dipeptides, the new compounds of the formula (I) have other additional improvements in quality:

Balb/c mice are immunised by intraperitoneal injection of $2 \times 10^4$ P815 mastocytoma cells on day 0. On day 15 the splenocytes of the animals so immunised are examined in vitro for the presence of cytotoxic T-lymphocytes directed against P815 mastocytoma cells. For this purpose, the P815 target cells are labelled with $^{51}Cr$ and the extent of the cytotoxic reaction is ascertained by measuring the radioactivity in the culture supernatant. In the dose used, the P815 mastocytoma cells are subimmunogenic for the recipient mice, that is to say, they induce no, or only a very negligible, formation of cytotoxic T-cells. Simultaneous intraperitoneal administration of from 1 to 50 μg of the mentioned muramyl peptides of the formula I leads to a significant increase in the formation of cytotoxic T-cells (by a factor of 10 to 30 compared with untreated mice).

The immunopotentiating properties of the novel compounds of the formula (I) can also be demonstrated in mice in the case of the induction of specific immunotolerance to transplant antigens by immunisation with autoblasts to which an adjuvant has been added:

In a mixed lymphocyte culture, splenolymphocytes of the prospective transplant recipient (C57 Bl/6J mice) are incubated with irradiated splenocytes of the prospective transplant donor (CBA/J mice). T-lymphocytes having specific receptors for the histocompatibility antigens of the donor proliferate and become blast cells; these can be separated from the other cells by sedimentation. The specific blast cells express the relevant idiotypic specificities of the membrane receptors and, admixed with complete Freund's adjuvant (CFA), are injected into the prospective transplant recipients (C57 Bl/6J) as auto-immunogens for the induction of specific tolerance to the relevant transplant antigens. The immunisation is carried out four times at intervals of four weeks with autologous anti-CBA/J T-lymphoblasts. Adsorbates of T-autoblasts with the novel compounds of the formula (I) ($10^9$ blast cells are suspended in a solution of 20 mg of substance in 20 ml of PBS; after a two-hour incubation period the cells are centrifuged and washed twice with PBS) are able to induce specific immunotolerance in the absence of CFA, the adsorbates being as effective as the lymphoblasts in CFA.

The novel compounds of the formula (I) are also able, in concentrations of from 0.5 to 100 μg/ml in splenocyte cultures of normal mice, to induce the formation of antibody-producing cells (an increase in the 19S-plaque-forming cells by a factor of 10 to 30 above the control value [in the absence of the stimulating substances]): thus in the presence of the mentioned compounds, for example specific antibodies against sheep erythrocytes are formed, without sheep erythrocytes being added to the cultures for the immunisation. On the other hand, when compared with a normally thymus-dependent antigen (sheep erythrocytes), the mentioned substances, in the same concentration range, are also able to increase the immunological reactivity of T-cell-depleted splenocyte cultures (of congenitally athymic nu/nu mice) (by a factor of 10 to 30 compared with untreated control cultures). The mentioned compounds, however, in vitro directly or indirectly induce not only proliferation and synthesis of B-lymphocytes (i.e. of potential antibody-forming cells), but also impart effects to T-lymphocytes (to which regulatory active promotor and suppressor cells and also cytotoxic effector cells belong). Thus, for example, the mentioned compounds in a concentration range of from 1 to 20 μg/ml are able considerably to potentiate the reactivity of cortisone-resistant thymus cells compared with allogenic irradiated stimulator lymphocytes (up to 10 times).

The above-mentioned effects are probably indirectly brought about in that such lipophilic muramyl peptides activate macrophages, which in turn promote the reactivity of T- and B-lymphocytes. In fact, it can be shown that the mentioned compounds, even in small concentrations (0.5 to 10 μg/ml), liberate large amounts of "colony stimulating activity" (CSA) from mouse-macrophages (induction of up to 150 to 200 colonies within 7 days from $10^5$ bone marrow cells of mice after the addition of 20% supernatant liquor from macrophage cultures incubated for 24 hours with the substance, compared with 0 to 5 colonies on the addition of supernatant liquors of untreated macrophase cultures). CSA is a biological mediator which is necessary for the differentiation of bone marrow parent cells from macrophages and polymorphonuclear leucocytes. The mentioned compounds in this way cause an increased supply of cells that are of prime importance for non-specific resistance and for the induction, amplification and expression of specific (lymphocyte-induced) immunoreactions.

The immunopotentiating action of the novel compounds can be demonstrated in vivo: the injection of a phospholipid derivative of the muramyl peptide according to the invention leads within 3 to 9 hours to a great increase in the CSA concentration in the serum (up to 120 colonies per $10^5$ bone marrow cells of mice after the addition of serum extracted with chloroform [5% final concentration] compared with 0 to 5 colonies in untreated animals). Correspondingly, by administration of the same compounds in vivo the ability of mice to form antibodies is considerably potentiated.

The immunopotentiating properties of the novel compounds of the formula I can also be demonstrated in tumour models, for example the Ehrlich ascites tumour in the mouse.

An intraperitoneal injection of $10^6$ syngenic Ehrlich ascites tumour cells in Balb/c mice leads on average in 18 days to the death of the animals. If the mice are injected intraperitoneally with $10^7$ (group 1), $10^6$ (group 2) and $10^5$ (group 3) ascites tumour cells which have been charged in vitro with the novel compounds of the formula I ($10^9$ ascites tumour cells are suspended in a solution of 40 mg of the test substance in 20 ml of phosphate-buffered physiological common salt solution (PBS) and after a two-hour incubation at 37° C. the cells are centrifuged and washed twice with PBS; the cells incorporate the test compound into their membrane during this treatment) then in 18 days no tumour growth has occurred. On the 19th day, $10^6$ native Ehrlich ascites tumour cells are administered intraperitoneally to each of the animals. The following effects are observed:
group 1: 8 of the 10 animals survive the 80th day,
group 2: 6 of the 10 animals survive the 80th day,
group 3: the animals die, like the control animals, after 18 days.

The compounds according to the present invention are additionally only slightly toxic: even intraperitoneal administration five times at a dose of 100 mg/kg/day on five successive days were tolerated by the mice apparently without symptoms. Because the doses required for immunostimulation are very small, the therapeutic scope of the novel compounds is very large.

The novel compounds according to the present invention can thus considerably increase the cellular and especially the humoral immunity, both in admixture with the antigen itself (adjuvant effect in the narrower sense) and when administered separately at a different time and at a different site from the antigen injection (systemic immunopotentiation).

The novel compounds according to the present invention may thus be used as adjuvants in admixture with vaccines to improve the success of vaccination and to improve the protection against infection imparted by humoral antibodies and/or cellular immunity against bacterial, viral or parasitic causative organisms.

Finally, the described compounds in admixture with different antigens are suitable as adjuvants in the experimental and industrial manufacture of antisera for therapy and diagnostics and in the induction of immunologically activated lymphocyte populations for cell transfer processes.

Moreover, the novel compounds can also be used, without simultaneous administration of antigens, to promote immune reactions in humans and animals that are already progressing subliminally. The compounds are accordingly particularly suitable for stimulating the body's defence mechanism, for example in the case of chronic and acute infections or in the case of selective (antigen-specific) immunological defects, and in hereditary and also in acquired general (i.e. not antigen-specific) immunological defective conditions, such as occur in old age, in the course of serious primary diseases and especially after therapy with ionising radiation or with hormones having an immunosuppressive action. The mentioned substances can thus be administered preferably also in combination with antibiotics, chemotherapeutic agents, or in other healing methods to combat immunological damage. Finally, the described substances are also suitable for general prophylaxis of infectious diseases in humans and animals.

The invention relates especially to compounds of the formula I in which X represents carbonyl, $R_1$ represents optionally substituted alkyl or aryl, $R_2$, $R_3$, $R_4$ and $R_6$ represent hydrogen or lower alkyl, $R_5$ represents hydrogen, lower alkyl optionally substituted by hydroxy, lower alkoxy, mercapto or lower alkylthio or halogen, or represents cycloalkyl or cycloalkyl-lower alkyl in each of which the cycloalkyl radical contains from 4 to 6 carbon atoms, optionally substituted phenyl or phenyl-lower alkyl, or heterocyclyl or heterocyclyl-lower alkyl each containing one or two nitrogen atoms, or $R_4$ and $R_5$ together also represent alkylene having 3 or 4 carbon atoms, $R_7$ represents hydrogen and one of the radicals $A_1$ and $A_2$ represents a radical of the formula

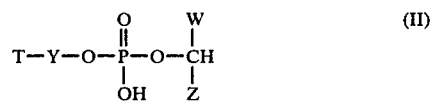

in which T represents -NH or -O, in which Y is optionally substituted alkylene which may also be interrupted by oxycarbonyl or iminocarbonyl, W represents hydrogen and Z represents a 1,2-dihydroxyethyl or 2-hydroxyethyl group, in which at least one of the hydroxy groups is esterified or etherified in the above specified manner, and the other of the radicals $A_1$ and $A_2$ represents hydroxy, lower alkoxy, amino, lower alkylamino or aminocarbonyl-lower alkylamino.

The invention relates especially to compounds of the formula I in which X represents carbonyl, $R_1$ represents lower alkyl optionally substituted by hydroxy, lower alkoxy or halogen, or represents phenyl optionally substituted by hydroxy, lower alkoxy, lower alkyl or halogen, $R_2$, $R_4$ and $R_6$ represent hydrogen, $R_3$ represents hydrogen or lower alkyl, $R_5$ represents hydrogen, lower alkyl having from 1 to 3 carbon atoms optionally substituted by hydroxy, lower alkoxy, mercapto, lower alkylthio or halogen, or represents cycloalkyl or cycloalkyl-lower alkyl in which the lower alkyl radical contains from 1 to 3 carbon atoms, and in each of which the cycloalkyl radical contains from 4 to 6 carbon atoms, phenyl or phenyl-lower alkyl having from 1 to 3 carbon atoms in the lower alkyl radical, each optionally substituted by hydroxy, lower alkoxy or halogen, or represents heterocyclyl or heterocyclyl-lower alkyl having 1 to 3 carbon atoms in the lower alkyl radical and each containing one or two nitrogen atoms and having 5 or 6 ring members, or $R_4$ and $R_5$ together also represent alkylene having 3 or 4 carbon atoms, $R_7$ represents hydrogen, and one of the radicals $A_1$ and $A_2$ represents a radical of the formula

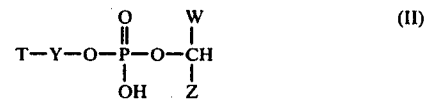

in which T represents -NH or -O, Y represents optionally substituted lower alkylene or a radical of the formula

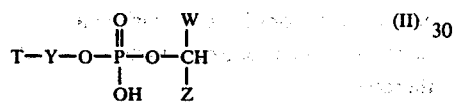

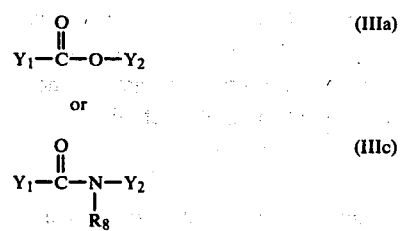

wherein $Y_1$ and $Y_2$ each represents optionally substituted lower alkylene and $R_8$ represents hydrogen, W represents hydrogen and Z represents a 1,2-dihydroxyethyl or 2-hydroxyethyl group in which at least one of the hydroxy groups is esterified by an aliphatic carboxylic acid having from 16 to 22 carbon atoms and optionally unsaturated once or twice, or by a natural or synthetic mycolic acid, or etherified by an aliphatic alcohol having from 12 to 18 carbon atoms and optionally unsaturated once or twice, and the other of the radicals $A_1$ and $A_2$ represents hydroxy, lower alkoxy, amino, lower alkylamino or aminocarbonyl-lower alkylamino.

The invention relates especially to compounds of the formula I in which X represents carbonyl, $R_1$ represents lower alkyl having from 1 to 3 carbon atoms or phenyl, $R_2$, $R_4$ and $R_6$ represent hydrogen, $R_3$ represents hydrogen or lower alkyl having from 1 to 3 carbon atoms, $R_5$ represents hydrogen, lower alkyl having from 1 to 3 carbon atoms optionally substituted by hydroxy, methoxy, mercapto, methylthio or halogen, or represents phenyl or phenylmethyl each optionally substituted by hydroxy, methoxy or halogen, or represents heterocyclyl or heterocyclylmethyl each containing one or two nitrogen atoms and having 5 ring members, or $R_4$ and $R_5$ together also represent trimethylene, $R_7$ represents hydrogen, and one of the radicals $A_1$ and $A_2$ represents a radical of the formula

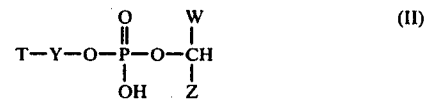

in which
T represents -NH or -O,
Y represents lower alkylene having 2 or 3 carbon atoms or a radical of the formula (IIIa) or (IIIc), wherein $R_8$ represents hydrogen and $Y_1$ and $Y_2$ independently of one another, each represents lower alkylene having from 1 to 3 carbon atoms optionally substituted by hydroxy, lower alkoxy, mercapto or lower alkylthio, or lower alkylene having from 1 to 3 carbon atoms substituted by optionally hydroxy-, methoxy- or halogen-substituted phenyl or phenyl-lower alkyl, or by heterocyclyl or heterocyclyl-lower alkyl containing one or two nitrogen atoms and having 5 or 6 ring members and from 1 to 3 carbon atoms in the lower alkyl radical,
W represents hydrogen and
Z represents a 1,2-dihydroxyethyl or 2-hydroxyethyl group in which at least one of the hydroxy groups is esterified by an aliphatic carboxylic acid having from 16 to 20 carbon atoms and optionally unsaturated once or twice, or etherified by an aliphatic alcohol having from 12 to 18 carbon atoms and optionally unsaturated once or twice,
and the other of the radicals $A_1$ and $A_2$ represents hydroxy, lower alkoxy, amino, lower alkylamino or aminocarbonyl-lower alkylamino.

Preferred are muramyl peptides of the formula I wherein X represents carbonyl, $R_1$ represents lower alkyl which is unsubstituted or substituted by hydroxy, lower alkoxy or by halogen; or phenyl which is unsubstituted or substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms which is unsubstituted or substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical which are unsubstituted or substituted in the phenyl-moiety by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

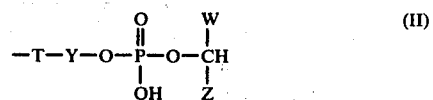

wherein T represents NH or O, Y represents optionally substituted lower alkylene or a radical of the formulae

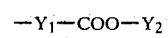  (IIIa)

or

  (IIIc)

in which $R_8$ represents hydrogen or methyl and each of $Y_1$ and $Y_2$ independently of the other represents lower alkylene that has from 1 to 7 carbon atoms and is unsubstituted or substituted by hydroxy, lower-alkoxy, mercapto, methylthio, phenyl, 4-imidazolyl or by 3-indolyl, W represents hydrogen and Z represents a 1,2-dihydroxyethyl or 2-hydroxyethyl group in which at least one hydroxy group is esterified by an aliphatic carboxylic acid having from 12 to 24 carbon atoms which is saturated or contains one or two double bonds, or by a natural or synthetic mycolic acid or etherified by an aliphatic alocohol having from 10 to 22 carbon atoms which is saturated or contains one or two double bonds, or each of W and Z represents a hydroxymethyl group esterified by an aliphatic carboxylic acid having from 12 to 24 carbon atoms which is saturated or contains one or two double bonds, or by a natural or synthetic mycolic acid or etherified by an aliphatic alcohol having from 10 to 22 carbon atoms which is saturated or contains one or two double bonds, and the other of the radicals $A_1$ and $A_2$ is hydroxy, lower alkoxy, amino, lower alkylamino or aminocarbonyl-lower alkylamino and salts thereof. other preferred muramyl peptides having formula I are those wherein $R_1$ represents lower alkyl having 1 to 3 carbon atoms or phenyl, $R_2$, $R_4$ and $R_6$ represent hydrogen, $R_3$ represents hydrogen or lower alkyl having 1 to 3 carbon atoms, $R_5$ represents hydrogen or lower alkyl, $R_7$ represents hydrogen, $A_1$ represents amino, lower alkylamino, hydroxy or lower alkoxy and $A_2$ represents a radical of the formula (II) according to claim 1, in which T represents -NH or -O, Y represents lower alkylene having 2 to 3 carbon atoms or a radical of the formula $CH_2$-CO-NH-$CH_2$-$CH_2$, W represents hydrogen and Z represents a 1,2-dihydroxyethyl group or 2-hydroxy-ethyl group in which one or two hydroxy groups are esterified by identical or different saturated or singly or doubly unsaturated alkane carboxylic acids having 16 to 22 carbon atoms or etherified by a saturated or singly or doubly unsaturated alkanol having 12 to 18 carbon atoms, or in which W and Z each represent a hydroxymethyl group which is esterified by a saturated or singly or doubly unsaturated alkane carboxylic acid having 16 to 22 carbon atoms or etherified by a saturated or singly or doubly unsaturated alkanol having 12 to 18 carbon atoms, and salts thereof.

Especially preferred are muramyl peptides of the formula I wherein X represents carbonyl, $R_1$ represents lower alkyl or phenyl, $R_2$, $R_6$ and $R_7$ represent hydrogen, $R_3$ and $R_4$ represent hydrogen or methyl, $R_5$ represents lower alkyl having from 1 to 4 carbon atoms, $A_1$ represents amino and $A_2$ represents a radical of the formula

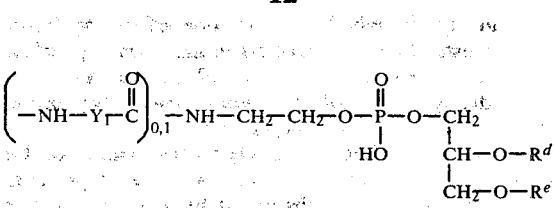

wherein $Y_1$ represents a radical of one of the formulae

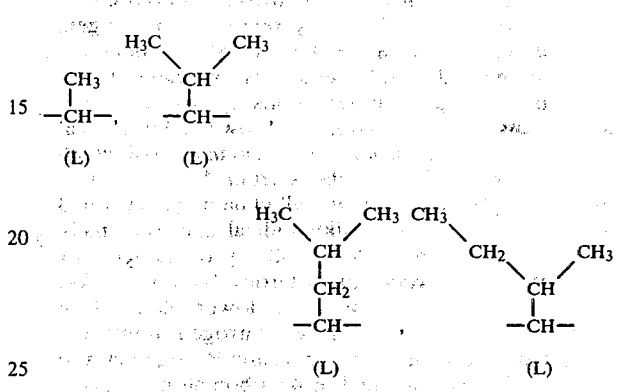

and $R^d$ and $R^e$ independently of one another represent the acyl radical of an unsubstituted aliphatic carboxylic acid having from 12 to 22 carbon atoms, which is saturated or contains one or two double bonds, and the salts thereof.

Most especially preferred are muramyl peptides of the formula I
in which
X represents carbonyl,
$R_1$ represents methyl, ethyl or phenyl,
$R_2$, $R_6$ and $R_7$ represent hydrogen,
$R_3$ and $R_4$ represent hydrogen or methyl,
$R_5$ represents methyl or ethyl,
$A_1$ represents amino
and
$A_2$ represents a radical of the formula

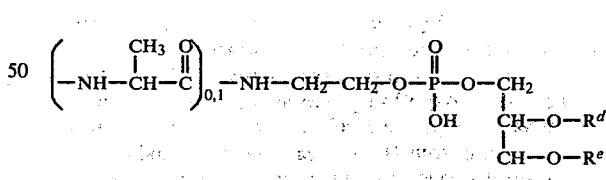

wherein $R^d$ and $R^e$ independently of one another represent the acyl radical of an unsubstituted and unbranched aliphatic carboxylic acid having from 12 to 22 carbon atoms, which is saturated or contains one or two double bonds, and the salts thereof.

The invention relates especially to the novel muramyl peptides described in the Examples.

The novel compounds of the formula I can be obtained according to methods known per se.

Thus, they can be obtained when a compound of the formula

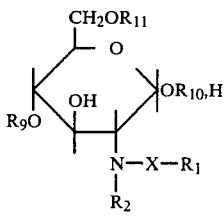

(V)

in which

X, $R_1$ and $R_2$ have the meanings given above and hydroxy groups optionally present therein are protected with a protecting group that can readily be split off, and $R_9$, $R_{10}$ and $R_{11}$ represent a protecting group that can readily be split off, or a metal compound thereof, is reacted with a compound of the formula

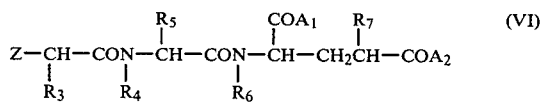

(VI)

in which

Z represents a reactively esterified hydroxy group, $R_3$, $R_4$, $R_5$, $R_6$, $R_7$, $A_1$ and $A_2$ have the meanings given above and hydroxy groups optionally present therein are protected by a protecting group that can readily be splitt off, and protecting groups present are split off.

A reactively esterified hydroxy group is especially a hydroxy group esterified by a strong inorganic or organic acid, especially a hydroxy group that has been esterified by hydrohalic acid, such as hydrochloric, hydrobromic or especially hydriodic acid.

A metal compound is especially a corresponding alkali metal derivative, for example a sodium or potassium derivative. It may be prepared, for example, by treating a compound of the formula V with a suitable base, such as a corresponding alkali metal compound, such as sodium hydride, sodium amide or butyllithium.

Protecting groups that can readily be split off are those known from peptide and sugar chemistry. For hydroxy groups the following should be given special mention: acyl radicals, for example lower alkanoyl radicals, such as acetyl, aroyl radicals, such as benzoyl, and especially radicals derived from carbonic acid derivatives, such as benzyloxycarbonyl or lower alkoxycarbonyl, or alkyl, especially tert.-butyl, benzyl optionally substituted by nitro, lower alkoxy or by halogen, triphenylmethyl or tetrahydropyranyl each optionally substituted by halogen or by lower alkoxy such as methoxy, or optionally substituted alkylidene radicals that bond the oxygen atoms in the 4- and 6-position. Such alkylidene radicals are especially a lower alkylidene radical, especially the methylidene, isopropylidene or propylidene radical, or alternatively an optionally substituted benzylidene radical.

These protecting groups can be split off in a manner known per se. Thus, they can be removed by acid hydrolysis, and benzyl or benzylidene radicals also can be removed by hydrogenolysis, for example using hydrogen in the presence of a noble metal catalyst, such as a palladium or platinum catalyst.

The starting materials used are known or can be manufactured in a manner known per se.

The novel compounds can also be obtained when, in a manner known per se, a compound of the formula

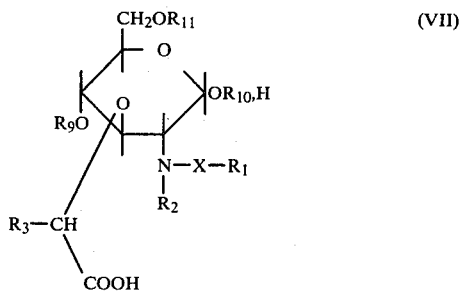

(VII)

in which

X, $R_1$, $R_2$ and $R_3$ have the meanings given above, and $R_9$, $R_{10}$ and $R_{11}$ represent hydrogen or a protecting group that can readily be split off, or a derivative thereof is codensed with a compound of the formula

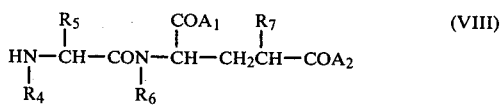

(VIII)

in which $R_4$, $R_5$, $R_6$, $R_7$, $A_1$ and $A_2$ have the meaning given above, provided that carboxy groups and, if desired, free hydroxy groups present in these radicals are protected by protecting groups that can readily be split off, or with a derivative thereof, and protecting groups present are split off.

The condensation is effected, for example, by reacting the acid (VII) in activated form with the amino compound (VIII), or reacting the acid (VII) with the compound (VIII), the amino group of which is present in the activated form. The activated carboxyl group may be, for example, an acid anhydride, preferably a mixed acid anhydride, for example with a carbonic acid lower alkyl ester, such as carbonic acid ethyl or isobutyl ester, an acid azide, an acid amide, such as an imidazolide, or an activated ester. Activated esters deserving special mention are: the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxy-phthalimide ester, 8-hydroxyquinoline ester, 2-hydroxy-1,2-dihydro-1-ethoxycarbonylquinoline ester, or N-hydroxypiperidine ester, or enol esters that are formed with N-ethyl-5-phenylisoxazolium 3'-sulphonate. Activated esters may also be obtained, if desired, with a carbodiimide with the addition of N-hydroxysuccinimide or with a 1-hydroxybenzotriazole or 3-hydroxy-4-oxo-3,4-dihydrobenzo[d]-1,2,3-triazine each unsubstituted or substituted, for example by halogen, methyl or methoxy.

The amino group is activated for example by reaction with a phosphite amide.

Among the methods of the reaction with activated acids, especially those with N-ethyl-5-phenylisoxazolium 3'-sulphonate (Woodward reagent K) or 2- ethoxy-1,2-dihydro-1-ethoxycarbonylquinoline or carbodiimide should be mentioned.

Protecting groups that can readily be split off are those that are known from peptide and sugar chemistry. For carboxy groups, special mention should be given to tertiary butyl, benzyl or benzhydryl and, for hydroxy groups, to acyl radicals, for example lower alkanoyl radicals such as acetyl, aroyl radicals, such as benzoyl, and especially radicals derived from carbonic acid derivatives, such as benzyloxycarbonyl or lower alkoxycarbonyl, or alkyl, especially tert.-butyl, benzyl optionally substituted by nitro, lower alkoxy or by halogen, triphenylmethyl or tetrahydropyranyl each optionally substituted by halogen or by lower alkoxy, such as methoxy, or optionally substituted alkylidene radicals that bond the oxygen atoms in the 4- and 6-position of the sugar moiety. Such alkylidene radicals are especially a lower alkylidene radical, especially the methylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known or can be manufactured in a manner known per se.

Another process method of manufacturing these novel compounds consists in condensing a compound of the formula

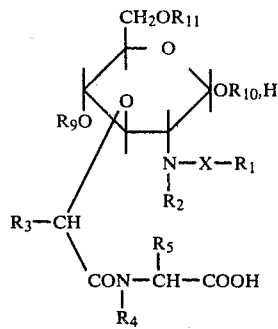
(IX)

in which
X, $R_1$, $R_2$, $R_3$, $R_4$ and $R_5$ have the meanings given above, provided that free hydroxy groups contained therein are optionally protected with a protecting group that can readily be split off, and
$R_9$, $R_{10}$ and $R_{11}$ represent hydrogen or protecting groups that can readily be split off,
or derivatives thereof, with a compound of the formula

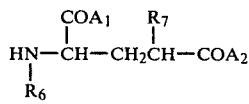
(X)

in which
$R_6$, $R_7$, $A_1$ and $A_2$ have the meanings given above, provided that free carboxyl groups present in the radicals $R_7$, $A_1$ and $A_2$ are protected by protecting groups that can readily be split off,
and splitting off protecting groups present.

The condensation is effected, for example by reaching the acid IX in activated form with the amino compound X, or reacting the acid IX with the compound X, the amino group of which is present in activated form. The activated carboxyl group can be, for example, an acid anhydride, preferably a mixed acid anhydride, an acid amide or an activated ester. Those which may be especially considered are the above-mentioned acid anhydrides, amides or esters. The amino group is activated for example by reaction with a phosphite amide.

The protecting groups that can readily be split off also correspond to those already mentioned above. They can be split off in a manner known per se: by acid hydrolysis, or, in the case of benzyl or benzylidene radicals, also by hydrogenolysis, for example with hydrogen in the presence of a noble metal catalyst, such as a palladium or platinum catalyst.

The starting materials can be obtained in a manner known per se. Thus, for example, corresponding sugars unsubstituted in the 3-position can be reacted with a halo-$R_3$-acetamido-$R_5$-acetic acid, or a compound of the formula VII can be reacted with an amino-$R_5$-acetic acid, the carboxyl group of which is protected in the manner indicated above, and the protecting groups can be split off.

Another process method for manufacturing these novel compounds in which T represents -NH, consists in condensing, in a manner known per se, a compound of the formula

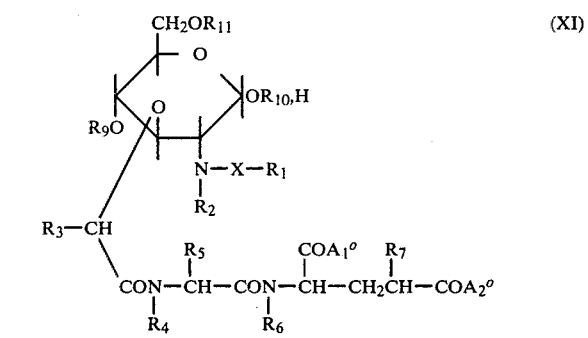
(XI)

in which
X, $R_1$, $R_2$, $R_3$, $R_4$, $R_5$, $R_6$ and $R_7$ have the meanings given above,
$R_9$, $R_{10}$ and $R_{11}$ represent hydrogen or a protecting group that can readily be split off, and
one of the radicals $A_1°$ and $A_2°$ represents an activated hydroxy group and the other represents etherified hydroxy, amino, lower alkylamino or aminocarbonyl lower alkylamino,
with a compound of the formula

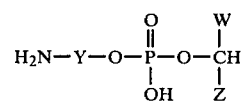
(XII)

in which
Y, W and Z have the meanings given above.

The activated carboxylic acid groups $COA_1°$ or $COA_2°$, respectively, may, for example, be an acid anhydride, for example with a carbonic acid lower alkyl ester, such as carbonic acid ethyl or isobutyl ester, an acid azide, an acid amide, such as an imidazolide or isoxazolide, or an activated ester. Activated esters deserving special mention are: the cyanomethyl ester, carboxymethyl ester, p-nitrophenylthio ester, methoxyethylthio ester, acetylaminoethylthio ester, p-nitrophenyl ester, 2,4,5-trichlorophenyl ester, N-hydroxy-succinimide ester, N-hydroxy-phthalimide ester, 8-hydroxy-quinoline ester and N-hydroxy-piperidine ester. Active esters may also be obtained, if desired, with a carbodiimide with the addition of N-hydroxysuccinimide, or a 1-hydroxybenzotriazole or 3-hydroxy-4-oxo-3,4-dihydrobenzo[d]-1,2,3-triazine each unsubstituted or substituted, for example by halogen, methyl or methoxy.

Preferred active esters are those with N-hydroxysuccinimide or the C-substitution products thereof, such as N-hydroxymethylsuccinimide or N-hydroxydimethylsuccinimide, or the reaction with a carbodiimide, such as carbodiimide itself or 1-ethyl-3-(3-dimethylaminopropyl)carbodiimide.

The starting materials used for this purpose are known or can be manufactured in a manner known per se.

If, in the novel compounds of the formula I, T represents -O, the compounds may also be obtained when, in a manner known per se, a compound of the formula

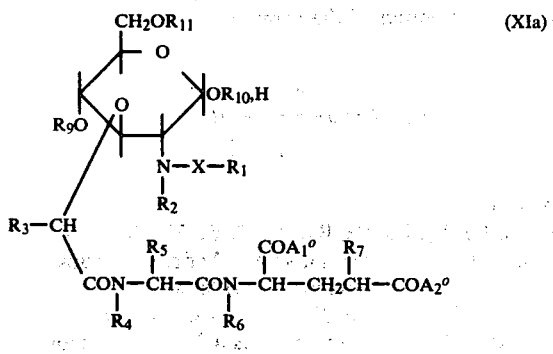

in which

X, $R_1$, $R_2$, $R_3$, $R_4$, $R_5$, $R_6$ and $R_7$ have the meanings given above, $R_9$, $R_{10}$ and $R_{11}$ represent hydrogen or a protecting group that can readily be split off, and one of the radicals $A_1°$ and $A_2°$ represents a hydroxy group and the other represents etherified hydroxy, amino, lower alkylamino or aminocarbonyl-lower alkylamino, is esterified in a manner known per se with a compound of the formula

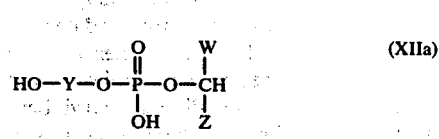

in which

Y, W and Z have the meanings given above, wherein the acid XIa or the alcohol XIIa is present in reactive form.

This reaction can be carried out by esterifying the free acid with the alcohol in the presence of an agent splitting off water, such as carbodiimide, for example dicyclohexylcarbodiimide, and an amine, such as pyridine or dimethylaminopyridine, or a trialkylamine, for example trimethylamine. Alternatively, the carboxylic acid may be reacted, for example in the form of a salt, such as the sodium or potassium salt, with a reactive ester of the alcohol, for example an ester with a strong inorganic or organic acid, such as a hydrohalic acid, for example hydrochloric, hydrobromic or hydriodic acid, or with an organic sulphonic acid, such as p-toluenesulphonic acid or methanesulphonic or ethanesulphonic acid.

Furthermore, it is also possible to react the alcohol optionally as a salt, for example the sodium or potassium salt, with an activated carboxylic acid. Activated carboxylic acids deserving special mention are anhydrides, especially mixed acid anhydrides, for example with a carbonic acid lower alkyl ester, such as carbonic acid ethyl or isobutyl ester, an acid azide or halide, or an activated ester, such as the cyanomethyl ester, carboxymethyl ester, p-nitrophenylthio ester, p-nitrophenyl ester, 2,4,5-trichlorophenyl ester, pentachlorophenyl ester, N-hydroxy-succinimide ester, N-hydroxy-phthalimide ester, 8-hydroxy-quinoline ester, 2-hydroxy-1,2-dihydro-1-ethoxycarbonylquinoline ester or N-hydroxy-piperidine ester, or enol esters that are obtained with N-ethyl-5-phenylisoxazolium-3'-sulphonate. Activated esters may also be obtained if desired with a carbodiimide with the addition of N-hydroxysuccinimide, or a 1-hydroxybenzotriazole or 3-hydroxy-4-oxo-3,4-dihydrobenzo[d]-1,2,3-triazine each unsubstituted or substituted, for example by halogen, methyl or methoxy.

Protecting groups that can readily be split off are those known from peptide and sugar chemistry. For carboxy groups special mention should be given to tertiary butyl, benzyl or benzhydryl, and, for hydroxy groups, to acyl radicals, for example lower alkanoyl radicals such as acetyl, aroyl radicals, such as benzoyl, and especially to radicals that are derived from carbonic acid, such as benzyloxycarbonyl or lower alkoxycarbonyl, or alkyl, especially tert.-butyl, benzyl optionally substituted by nitro, lower alkoxy or halogen, triphenylmethyl or tetrahydropyranyl each optionally substituted by halogen or lower alkoxy, such as methoxy, or optionally substituted alkylidene radicals that bond the oxygen atoms in the 4- and 6-positions. Such alkylidene radicals are especially a lower alkylidene radical, more especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as palladium or platinum catalyst.

Furthermore, it is also possible to obtain the novel compounds of the formula I in which X represents a carbonyl group and $R_2$ represents hydrogen, when, in a compound of the formula

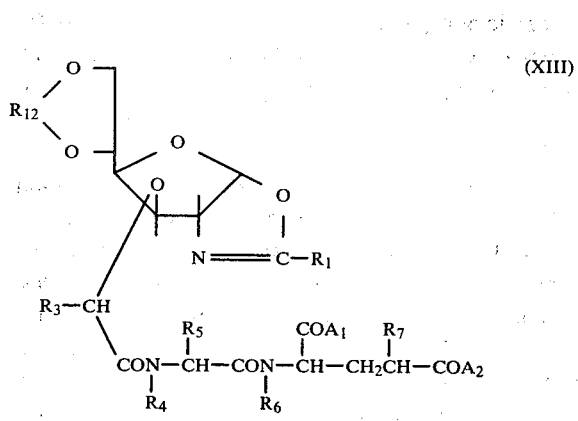

(XIII)

in which $R_1$, $R_3$, $R_4$, $R_5$, $R_6$, $R_7$, $A_1$ and $A_2$ have the meanings given above, and $R_{12}$ represents an alkylidene or cycloalkylidene group, the oxazoline and the dioxolane rings are split open by acid means and optionally present protecting groups are split off.

Alkylidene therein is especially lower alkylidene, such as isopropylidene, and cycloalkylidene is especially cyclopentylidene or cyclohexylidene.

This splitting is likewise carried out in a manner known per se, for example with an acidic ion exchanger, especially those with sulphonic acid groups such as Amberlite IR-120 (a styrene resin with strongly acidic sulpho groups) or Dowex 50 (polystyrenesulphonic acids) or with a strong inorganic or organic acid, such as hydrochloric acid, hydrobromic acid, sulphuric acid or a sulphonic acid, for example methanesulphonic acid, or with a phenylsulphonic acid optionally substituted in the aromatic ring, such as p-toluenesulphonic acid, or trifluoroacetic acid. If the operation is carried out in the presence of water, a free hydroxy group is obtained in the 1-position. If also one of the carboxyl groups $A_1$ or $A_2$ and/or $R_7$ is esterified by an alcohol, especially a lower alkanol, it can be saponified, especially at elevated temperature, with aqueous acid.

In the resulting compounds, protecting groups at the peptide radical can be split off subsequently, for example by hydrogenolysis, for example with catalytically activated hydrogen, or by hydrolysis.

The starting materials used therein can be obtained, for example, when the $R_3$-acetamido peptide radical is introduced in one or more stages into a corresponding oxazoline with a free hydroxy group in the 3-position of the sugar radical.

Compounds of the formula I in which Y represents a radical of the formula IIIc or IIId, can also be obtained by condensing a compound of the formula

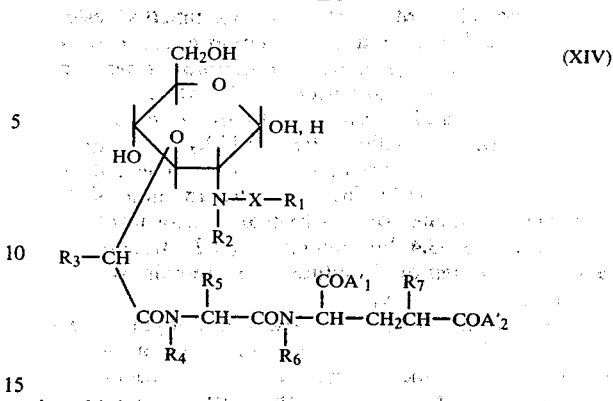

(XIV)

in which
one of the radicals $A_1'$ and $A_2'$ represents a radical of the formula

$$-T-Y_1-M_1 \qquad (XV)$$

and the other of the radicals $A_1'$ and $A_2'$ represents etherified hydroxy or amino, lower alkylamino or aminocarbonyl-lower alkylamino, with a compound of the formula

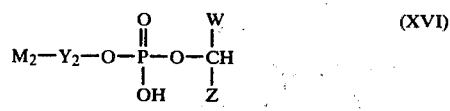

(XVI)

in which
X, $R_1$, $R_2$, $R_3$, $R_4$, $R_5$, $R_6$, $R_7$, T, $Y_1$, $Y_2$, W and Z have the meanings given above and hydroxy groups present therein are optionally protected by protecting groups that can readily be split off, and one of the radicals $M_1$ and $M_2$ represents a free amino group or an activated derivative thereof, and the other represents a carboxylic acid group or an activated derivative thereof,
and splitting off optionally present protecting groups.

Protecting groups that can readily be split off are those that are known from peptide and sugar chemistry. For carboxy groups, special mention should be given to tertiary butyl, benzyl, triphenylmethyl or benzhydryl both optionally substituted by halogen or by lower alkoxy, such as methoxy, and, for hydroxy groups, to acyl radicals, for example lower alkanoyl radicals such as acetyl, aroyl radicals, such as benzoyl, and especially radicals derived from carbonic acid, such as benzyloxycarbonyl or lower alkoxycarbonyl, or alkyl, especially tert.-butyl, benzyl or tetrahydropyranyl both optionally substituted by nitro, lower alkoxy or by halogen, or optionally substituted alkylidene radicals that bond the oxygen atoms in the 4- and 6-position. Such alkylidene radicals are especially a lower alkylidene radical, especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known or can be manufactured in a manner known per se.

The condensation is carried out, for example, by reacting the compound (XIV) in the form of the activated carboxylic acid with the amino compound (XVI), or reacting the acid (XIV) with the compound (XVI) of which the amino group is present in activated form. The activated carboxyl group may be, for example, an acid anhydride, preferably a mixed acid anhydride, such as, for example, with a carbonic acid lower alkyl ester, such as carbonic acid ethyl or isobutyl ester, an acid azide, an acid amide, such as an imidazolide or isoxazolide, or an activated ester. Activated esters are especially the cyanomethyl ester, carboxymethyl ester, p-nitrophenylthio ester, p-nitrophenylester, 2,4,5-trichlorophenyl ester, pentachlorophenyl ester, N-hydroxy-succinimide ester, N-hydroxy-phthalimide ester, 8-hydroxy-quinoline ester, 2-hydroxy-1,2-dihydro-1-ethoxycarbonylquinoline ester or N-hydroxypiperidine ester, or enol esters that have been obtained with N-ethyl-5-phenylisoxazolium 3'-sulphonate. Activated esters can also, if desired, be obtained with a carbodiimide with the addition of N-hydroxysuccinimide, or a 1-hydroxybenzotriazole or 4-oxo-3,4-dihydrobenzo[d]-1,2,3-triazine each unsubstituted or substituted, for example by halogen, methyl or methoxy.

The amino group is activated for example by reaction with a phosphite amide.

Among the methods of the reaction with activated acids, those with N-ethyl-5-phenylisoxazolium 3'-sulphonate (Woodward reagent K) or 2-ethoxy-1,2-dihydro-1-ethoxycarbonylquinoline or carbodiimide deserve special mention.

Compounds of the formula I in which Y represents a radical of the formula IIIa or IIIb may also be obtained when a compound of the formula

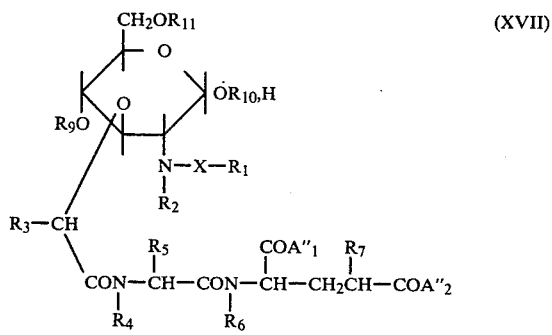

(XVII)

in which one of the radicals $A_1''$ and $A_2''$ represents a radical of the formula

$T-Y_1-M_3$  (XVIII)

is esterified in a manner known per se with a compound of the formula

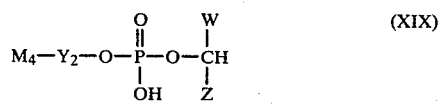

(XIX)

in which $X, R_1, R_2, R_3, R_4, R_5, R_6, R_7, T, Y_1, Y_2, W$ and $Z$ have the meanings given above, and hydroxy groups optionally present therein are protected by protecting groups that can readily be split off, $R_9$, $R_{10}$ and $R_{11}$ represent protecting groups that can readily be split off, and the other of the radicals $A_1''$ and $A_2''$ represents etherified hydroxy, amino, lower alkylamino or aminocarbonyl-lower alkylamino, and one of the radicals $M_3$ and $M_4$ represents a free hydroxy group and the other represents a free carboxyl group, one of the two radicals $M_3$ and $M_4$ optionally being present in reactive form.

This reaction can be carried out by esterifying the free acid with an alcohol in the presence of an agent splitting off water, such as a carbodiimide, for example dicyclohexylcarbodiimide, and an amine, such as pyridine, dimethylaminopyridine, or a trialkylamine, for example trimethylamine. Alternatively, the carboxylic acid may be reacted, for example in the form of a salt, with a reactive ester of the alcohol, for example an ester with a strong inorganic or organic acid, such as a hydrohalic acid, for example hydrochloric, hydrobromic or hydriodic acid, or with an organic sulphonic acid, such as p-toluenesulphonic acid or methanesulphonic or ethanesulphonic acid.

Futhermore, it is also possible to react the alcohol optionally as a salt, for example the sodium or potassium salt, with an activated carboxylic acid. Activated carboxylic acids are especially anhydrides, especially mixed acid anhydrides, for example with a carbonic acid lower alkyl ester, such as carbonic acid ethyl or isobutyl ester, an acid azide or halide or an activated ester, such as the cyanomethyl ester, carboxymethyl ester, p-nitrophenylthio ester, p-nitrophenyl ester, 2,4,5-trichlorophenyl ester, pentachlorophenyl ester, N-hydroxysuccinimide ester, N-hydroxyphthalimide ester, 8-hydroxyquinoline ester, 2-hydroxy-1,2-dihydro-1-ethoxycarbonylquinoline ester or N-hydroxypiperidine ester, or enol esters that are obtained with N-ethyl-5-phenylisoxazolium 3'-sulphonate. Activated esters can also be obtained, if desired, with a carbodiimide with the addition of N-hydroxysuccinimide, or a 1-hydroxybenzotriazole or 3-hydroxy-4-oxo-3,4-dihydrobenzo[d]-1,2,3-triazine each unsubstituted or substituted, for example by halogen, methyl or methoxy.

Protecting groups that can readily be split off are those known from peptide and sugar chemistry. For carboxy groups special mention should be given to tertiary butyl, benzyl, or triphenylmethyl or benzhydryl both optionally substituted by halogen or by lower alkoxy, such as methoxy, and, for hydroxy groups, to acyl radicals, for example lower alkanoyl radicals, such as acetyl, aroyl radicals such as benzoyl, and especially radicals derived from carbonic acid, such as benzyloxycarbonyl or lower alkoxycarbonyl, or alkyl, especially tert.-butyl, benzyl or tetrahydropyranyl both optionally substituted by nitro, lower alkoxy or by halogen, or optionally substituted alkylidene radicals that bond the oxygen atoms in the 4- and 6-position. Such alkylidene radicals are especially a lower alkylidene radical, especially the ethylidene, isopropylidene or propylidene radical, or alternatively an optionally substituted benzylidene radical, preferably substituted in the p-position.

These protecting groups can be split off in a manner known per se. Thus, they can be removed by acid hydrolysis, and benzyl or benzylidene radicals can also be removed by hydrogenolysis, for example with hydrogen in the presence of a noble metal catalyst, such as a palladium or platinum catalyst.

The starting materials used are known and can be manufactured in a manner known per se.

A further process method for the manufacture of the novel compounds of the formula I consists in reacting a compound of the formula $$
\begin{array}{c}
\text{CH}_2\text{OR}_{11} \\
\text{R}_9\text{O} \underset{\text{O}}{\overset{\text{O}}{\diamond}} \text{OR}_{10}, \text{H} \\
\text{N-X-R}_1 \\
| \\
\text{R}_2 \\
\text{R}_3\text{-CH} \\
\quad\quad \text{R}_5 \quad\quad \text{COA}_1''' \quad \text{R}_7 \\
\text{CON-CH-CON-CH-CH}_2\text{CH-COA}_2''' \\
| \quad\quad\quad\quad | \\
\text{R}_4 \quad\quad\quad \text{R}_6
\end{array}
\quad (XX)
$$

in which
X, $R_1$, $R_2$, $R_3$, $R_4$, $R_5$, $R_6$ and $R_7$ have the meanings given above, and hydroxy groups optionally present therein are protected with a protecting group that can readily be split off,
$R_9$, $R_{10}$ and $R_{11}$ represent protecting groups that can readily be split off, and
one of the radicals $A_1'''$ and $A_2'''$ represents T-Y-OH in which Y and T have as well as the other of the radicals $A_1'''$ and $A_2'''$ the meanings given above,
with a compound yielding the radical of the formula $$
\begin{array}{c}
\text{M}_5 \quad \text{W} \\
\parallel \quad | \\
-\text{P}-\text{O}-\text{CH} \\
| \quad\quad | \\
\text{OH} \quad\quad \text{Z}
\end{array}
\quad (XXI)
$$

in which
$=M_5$ represents a pair of electrons or oxo,
if $=M_5$ represents a pair of electrons, oxidising with a weak oxidising agent, and splitting off protecting groups present.

As compounds yielding a radical of the formula XXI, compounds of the formula $$
\begin{array}{c}
\text{M}_5 \quad \text{W} \\
\parallel \quad | \\
\text{M}_7-\text{P}-\text{O}-\text{CH} \\
| \quad\quad | \\
\text{OM}_6 \quad\quad \text{Z}
\end{array}
$$

in which
W, Z and $=M_5$ have the meanings given above,
$M_6$ represents hydrogen or a protecting group that can readily be splitt off, and
$M_7$ is optionally reactively modified hydroxy, should be especially mentioned.

If $M_6$ represents hydrogen and $=M_5$ represents a pair of electrons the compounds yielding a radical of the formula XXI are to a high percentage present in their tautomeric form, wherein $M_6$ is directly bonded to the phosphorus atom.

A protecting group $M_6$ that can readily be split off is especially lower alkoxy, such as methoxy or ethoxy, lower alkenyloxy, such as ethenyloxy or 1-methyl-propenyloxy, or benzyloxy.

An optionally reactively modified hydroxy group $M_7$ is especially the free hydroxy group, a hydroxy group esterified by a strong inorganic or organic acid, such as a hydroxy group esterified by a hydrohalic acid, a lower alkanecarboxylic acid or aryl- or alkylsulphonic acid, for example p-toluenesulphonic acid, methanesulphonic or ethanesulphonic acid. Alternatively, it may represent a phenoxy or lower alkoxy group.

This reaction is preferably carried out in the presence of an acid-binding agent, such as pyridine, a tri-lower alkylamine, for example triethylamine or trimethyl-amine, an imidazole, or an inorganic base, such as sodium or potassium hydroxide, or sodium or potassium alcoholate, an aprotic solvent, such as dimethyl sulphoxide or acetonitrile being preferred as solvent.

If, in the resulting compounds, $=M_5$ is a pair of electrons, oxidation is carried out, for example with a peracid, such as perbenzoic acid or with an alkyl hydrogen peroxide.

The splitting off of a protecting group $M_6$ usually takes place concurrently with splitting off of the remaining protecting groups. These can be removed in a manner known per se, for example by hydrogenolysis, for example with hydrogen in the presence of a noble metal catalyst, such as a palladium or platinum catalyst, or by acid hydrolysis.

The starting materials are known and can be manufactured in a manner known per se, for example by one of the above-mentioned suitably modified methods.

Furthermore, the novel compounds of the formula I can also be manufactured when a compound of the formula $$
\begin{array}{c}
\text{CH}_2\text{OR}_{11} \\
\text{R}_9\text{O} \underset{\text{O}}{\overset{\text{O}}{\diamond}} \text{OR}_{10}, \text{H} \\
\text{N-X-R}_1 \\
| \\
\text{R}_2 \\
\text{R}_3\text{-CH} \\
\quad\quad \text{R}_5 \quad\quad \text{COA}_1'''' \quad \text{R}_7 \\
\text{CON-CH-CON-CH-CH}_2\text{CH-COA}_2'''' \\
| \quad\quad\quad\quad | \\
\text{R}_4 \quad\quad\quad \text{R}_6
\end{array}
\quad (XXIII)
$$

in which
X, $R_1$, $R_2$, $R_3$, $R_4$, $R_5$, $R_6$, $R_7$ have the meanings given above, and hydroxy groups optionally present therein are protected by a protecting group that can readily be split off,
$R_9$, $R_{10}$ and $R_{11}$ represent protecting groups that can readily be split off, and one of the radicals $A_1''''$ and $A_2''''$ represents $$
\begin{array}{c}
\text{M}_5 \\
\parallel \\
-\text{T}-\text{Y}-\text{O}-\text{P}-\text{M}_7 \\
| \\
\text{OM}_6
\end{array}
\quad (XXIV)
$$

and the other represents free or etherified hydroxy, amino, lower alkylamino or aminocarbonyl-lower alkylamino,
wherein T, Y, $M_5$, $M_6$ and $M_7$ have the meanings given above, is reacted with a compound of the formula

(XXV)

in which

W and Z have the meanings given above, if =M₅ is a pair of electrons is oxidised with a weak oxidising agent and protecting groups present are split off.

A protecting group M₆ that can readily be split off is especially lower alkoxy, such as methoxy or ethoxy, lower alkenyloxy, such as ethenyloxy or 1-methylpropenyloxy, or benzyloxy.

An optionally reactively modified hydroxy group M₇ is especially the free hydroxy group, a hydroxy group esterified by a strong acid, such as a hydroxy group esterified by a hydrohalic acid, a nitroalkanecarboxylic acid or an arylsulphonic or alkylsulphonic acid, for example p-toluenesulphonic acid, methanesulphonic or ethanesulphonic acid. Alternatively, it may also represent a phenoxy or lower alkoxy group.

This reaction is preferably carried out in the presence of an acid-binding agent, such as pyridine, a trilower alkylamine, for example triethylamine or trimethyamine, an imidazole or an inorganic base, such as sodium or potassium hydroxide or sodium or potassium alcoholate, an aprotic solvent, such as dimethyl sulphoxide or acetonitrile being preferred as solvent.

If, in the resulting compounds M₅ is an electron pair, oxidation is carried out, for example, with a peracid, such as perbenzoic acid, or an alkyl hydrogen oxide.

The splitting off of a protecting group M₆ usually takes place concurrently with splitting off of the remaining protecting groups. These can be removed in a manner known per se, for example by hydrogenolysis, for example with hydrogen in the presence of a noble metal catalyst, such as a palladium or platinum catalyst, or by acid hydrolysis.

The starting materials are known and can be manufactured in a manner known per se, for example by one of the above-mentioned suitably modified methods.

Furthermore, the compounds of the formula I can also be obtained in that a compound of the formula

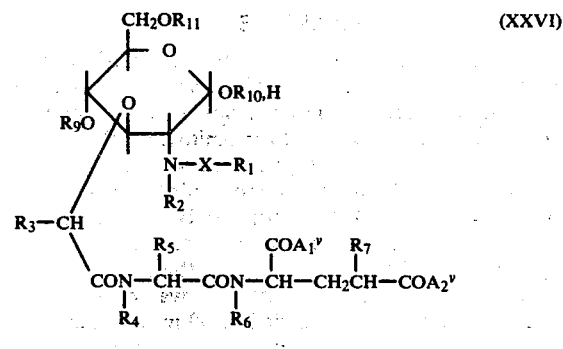
(XXVI)

in which

X, R₁, R₂, R₃, R₄, R₅, R₆ and R₇ have the meanings given above and hydroxy groups optionally present therein are protected by a protecting group that can readily be split off, R₉, R₁₀ and R₁₁ represent protecting groups that can readily be split off and one of the radicals A₁ᵛ and A₂ᵛ represents

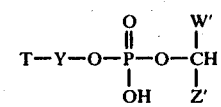

wherein W' and Z' have the same meanings as W and Z defined above subject to the condition that at least one hydroxyl group is present in free form, and the other radical A₁ᵛ or A₂ᵛ represents free or etherified hydroxy, amino, lower alkylamino or aminocarbonyl-lower alkylamino, is esterified by an optionally unsaturated long-chained aliphatic carboxylic acid or etherified by an optionally unsaturated long-chained aliphatic alcohol, and the protecting groups are split of.

The esterification, like the etherification, is effected in a manner known per se thus using preferably the long-chained acid and the long-chained alcohol in the form of a reactive derivative, such as an anhydride, preferably a mixed anhydride, for example with a hydrohalic acid, or in the form of an ester, similarly, for example, with a hydrohalic acid.

The splitting off of the protecting groups, which correspond to those mentioned above, can be carried out in the usual manner, especially by hydrogenolysis or by acid hydrolysis.

The starting materials can be manufactured, for example, according to one of the above-mentioned, suitably modified methods.

The processes described above are carried out according to methods known per se in the absence or preferably in the presence of diluents or solvents, if necessary while cooling or heating, at elevated pressure and/or in an inert gas atmosphere, such as a nitrogen atmosphere.

Taking into consideration all the substituents present in the molecule, especially mild reaction conditions should, if necessary, be applied, especially when readily hydrolysable O-acyl radicals are present, such as short reaction times, the use of mild acidic or basic agents in low concentrations, stoichiometric quantitative ratios, the selection of suitable catalysts, solvents, temperature and/or pressure conditions.

The invention relates also to those embodiments of the process in which a compound obtainable as an intermediate at any stage of the process is used as starting material and the remaining process steps are carried out, or the process is discontinued at any stage, or a starting material is formed under the reaction conditions or is used in the form of a reactive derivative or salt. The starting materials used are preferably those which according to the process result in the compounds described above as being especially valuable.

As outlined above, in the compounds of the formula I the proton bonded to the phosphorus atom via an oxygen atom can readily be split off by bases. As is exemplified in example 13, by dialysis of the aqueous solution of compounds of the formula I having no further acidic or basic groups, like carboxylic or amino groups respectively, against alkali metal phosphate buffer solution pH 7, a mixture of the alkali metal salts and the free acids is obtained, wherein the salts are present in an amount of approximately 40 to 90% as evidenced by elemental analysis (e.g. sodium analysis by flame photometry). However, the standard error allowing also for one sodium ion per molecule in accordance with theoretical considerations which suggest that the product resulting from the procedure described above at pH 7 should be present practically quantitatively in the form of the alkali metal salts.

In general, for the manufacture of the compounds of the formula I and their salts the pH value is of great importance and should be kept within approximately 3.5 and 7.5, especially between 5.5 and 7.5 if the process step takes more than a few hours. Dialysis against a suitable buffered solution or treatment with a suitable ionexchanger can not only be used for the manufacture of alkali metal salts but also for the manufacture of the other salts mentioned above.

The present invention relates likewise to pharmaceutical preparations that contain pharmaceutically acceptable salts, especially e.g. sodium salts, of compounds of the formula I or mixtures of the free phosphoric acids of the formula I and such salts. The pharmaceutical preparations according to the invention are those for enteral, such as oral, nasal or rectal, administration or preferably for parenteral administration to warm-blooded animals and which contain the pharmacological active substance alone or together with a pharmaceutically acceptable carrier. The dosage of the active substance depends on the species of warmblooded animal, the age and the individual condition, the kind of disease and also on the method of administration.

The substances of formula (I), e.g. N-Acetyl-muramyl-L-alanyl-D-isoglutaminyl-L-alanyl-2-(1′,2′-O-dipalmitoyl-sn-glycero-3′-hydroxyphosphoryloxy)-ethylamide and especially the pharmaceutically acceptable salts thereof, can e.g. be applied together with liposomes in order to prevent the formation of metastasis after operative removal of a primary tumor. In this case the daily dosage applied intravenously at the same time to warm-blooded animals of about 70 kg body weight, e.g to man, is about 0.01 to about 0.5 mg.

For the preparation of liposomes egg-, soya- or synthetic lecithins in admixture with cholesterine can be used. Especially are to be mentioned a mixture consisting of 1-palmitoyl-2-oleoyl-phosphatidylcholin and phosphatidylserin as well as a mixture consisting of pure egg phosphatidylcholine and beef brain phosphatidylserine (molar ratio 7:3).

The novel pharmaceutical preparations contain from approximately 10% to approximately 95%, preferably from approximately 20% to approximately 90%, of the active substance. The pharmaceutical preparations according to the invention may, for example, be in unit dose form, such as dragees, tablets, capsules, suppositories or ampoules.

The pharmaceutical preparations of the present invention are prepared in a manner known per se, for example by means of conventional mixing, granulating, coating, dissolving or lyophilising processes. In addition to the types of administration mentioned above pharmaceutical preparations especially for oral administration can also be obtained by combining the active substance with solid carriers, if desired granulating a resulting mixture and processing the mixture or granulate, if desired or necessary after the addition of suitable adjuncts, to form tablets or dragee cores. They may also be incorporated in synthetic carriers which release the active substances in doses or allow them to diffuse.

Suitable carriers are especially fillers, such as sugars, for example lactose, saccharose, mannitol or sorbitol, cellulose preparations and/or calcium phosphates, for example tri-calcium phosphate or calcium hydrogen phosphate, also binders, such as starch pastes, using, for example, maize, wheat, rice or potato starch, gelatin, tragacanth, methylcellulose, hydroxypropylmethylcellulose, sodium carboxymethylcellulose and/or polyvinylpyrrolidone, and/or, if desired, disintegrating agents, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talcum, stearic acid or salts thereof, such as magnesium or calcium stearate, and/or polyethylene glycol. Dragée cores are provided with suitable coatings which may optionally be resistant to gastric juices, there being used, inter alia, concentrated sugar solutions, which optionally contain gum arabic, talcum, polyvinylpyrrolidone, polyethylene glycol and/or titanium dioxide, and lacquer solutions in suitable organic solvents or solvent mixtures, or, for the preparation of coatings resistant to gastric juices, solutions of suitable cellulose preparations, such as acetylcellulose phthalate or hydroxypropylmethylcellulose phthalate. Colouring substances or pigments may be added to the tablets or dragée coatings, for example for identification or for indicating different doses of active substance.

The following Examples illustrate the above-described invention; they are not intended, however, to limit the scope thereof in any way. Temperatures are given in degrees Centigrade.

The compounds according to the invention of the formula I cannot be characterised by a melting point nor are spectroscopic data such as NMR and IR spectra suitable for satisfactory characterisation.

Furthermore, $R_f$ values are also unsuitable for precise characterisation because of the dominating nature of the lipid moieties.

Since, however, the structure of the starting materials is known exactly (cf. German Offenlegungsschrift 26 55 500; the particular phospholipid components used are commercially available) and since the linking of phopholipid and muramyl peptide is clear, the sequence of the building blocks in the end product and the structure thereof is therefore also clearly defined.

The compounds of the formula I which are described in the following examples 1 to 12 are present in admixture (about 1:1) with the corresponding triethylammonium salts.

EXAMPLE 1

A solution of 2 mmol of N-acetylmuramyl-L-alanyl-D-isoglutamine-N-hydroxysuccinimide ester in 6.5 ml of dimethylacetamide is added dropwise to a solution of 1.4 mmol of 2-(1′,2′-O-dipalmitoyl-sn-glycero-3′-hydroxyphosphoryloxy)ethylamine and of 2.5 mmol of triethylamine in 25 ml of a mixture of chloroform/methanol/water, 65:25:4. After stirring for 18 hours at 20° C., the solution is concentrated at reduced pressure to approximately 15 ml; in the course of this an emulsion is formed. This is diluted with 200 ml of water and freeze-dried. The residue is suspended in 30 ml of water and extensively dialysed against water. The inner dialysate, which contains the desired product, is freeze-dried. N-Acetylmuramyl-L-alanyl-D-isoglutaminyl-2-(1′,2′-O-dipalmitoyl-sn-glycero-3′-hydroxyphosphoryloxy)ethylamide is purified by chromatography over a Sephadex LH-20 column. Eluant mixture: chloroform/methanol/acetic acid/water, 25:15:4:2. In a thin layer chromatogram over silica gel the compound has the following $R_f$ values: 0.31 (in chloroform/methanol/water, 65:25:4) and 0.64 (in chloroform/methanol/acetic acid/water, 25:15:4:2).

The novel compound is characterised analytically by quantitative determination of the building blocks (N-acetyl.nuramic acid, palmitic acid, phosphate, L-alanine and D-glutamic acid):

N-acetylmuramic acid is determined by spectrophotometry by means of the Morgan-Elson reaction according to the modification by J. M. Ghuysen et al. [in "Methods in Enzymology" 8, 629 (1966)].

Phosphate is quantitatively determined according to Lowry et al. [J. Biol. Chem. 207, 1 (1954)].

Palmitic acid and the amino acids are quantitatively determined in a total hydrolysate (6 N HCl, 24 hours 110° C.) by gas chromatography or by means of an amino acid analyser using pentadecanoic acid or norleucine as internal standards.

The molar ratios found, calculated on phosphate, are as follows:

$PO_4'''$:N-acetylmuramic acid:L-alanine:D-glutamic acid:palmitic acid = 1:0.92:0.91:0.95:2.18.

The N-acetylmuramyl-L-alanyl-D-isoglutamine-N-hydroxysuccinimide ester used as starting material may be produced, for example, as follows:

2 mmol of N-acetylmuramyl-L-alanyl-D-isoglutamine, 2.2 mmol of N-hydroxysuccinimide and 2.2 mmol of dicyclohexylcarbodiimide are dissolved in 6.5 ml of dimethylacetamide and the solution is stirred for 18 hours at 20° C. The precipitated dicyclohexylurea is separated off and the solution is used directly for the condensation with the phospholipid.

The 2-(1',2'-O-dipalmitoyl-sn-glycero-3'-hydroxyphosphoryloxy)ethylamine used as starting material is a commercially available synthetic preparation.

EXAMPLE 2

N-acetyldemethylmuramyl-L-alanyl-D-isoglutaminyl-2-(1',2'-O-dipalmitoyl-sn-glycero-3'-hydroxyphosphoryloxy)ethylamide is obtained analogously to the manner described in Example 1 using 2-(1',2'-O-dipalmitoyl-sn-glycero-3'-hydroxyphosphoryloxy)ethylamine and N-acetyldemethylmuramyl-L-alanyl-D-isoglutamine-N-hydroxysuccinimide ester as starting materials;

$R_f$ values (over silica gel) as follows:

0.29 (in chloroform/methanol/water, 65:25:4), and 0.65 (in chloroform/methanol/acetic acid/water, 25:15:4:2).

EXAMPLE 3

N-acetylmuramyl-L-alanyl-D-isoglutaminyl-γ-oxymethylcarbonyl-2-(1',2'-O-dipalmitoyl-sn-glycero-3'-hydroxyphosphoryloxy)ethylamide is obtained analogously to the manner described in Example 1 using 2-(1',2'-O-dipalmitoyl-sn-glycero-3'-hydroxyphosphoryloxy)ethylamine and the N-hydroxysuccinimide ester of N-acetylmuramyl-L-alanyl-D-isoglutamine-γ-carboxymethyl ester as starting materials.

The $R_f$ values of the compound in a thin layer chromatogram over silica gel are as follows: 0.28 (in chloroform/methanol/water, 65:25:4), and 0.68 (in chloroform/methanol/acetic acid/water, 25:15:4.2).

EXAMPLE 4

N-acetylmuramyl-L-alanyl-D-isoglutaminyl-L-alanyl-2-(1',2'-O-dipalmitoyl-sn-glycero-3'-hydroxyphosphoryloxy)ethylamide is obtained analogously to the manner described in Example 1 using 2-(1',2'-O-dipalmitoyl-sn-glycero-3'-hydroxyphosphoryloxy)ethylamine and N-acetylmuramyl-L-alanyl-D-isoglutaminyl-L-alanine-N-hydroxysuccinimide ester as starting materials. $R_f$ value in a thin layer chromatogram over silica gel: 0.3 (in chloroform/methanol/water, 65:25:4).

EXAMPLE 5

N-acetyldemethylmuramyl-L-alanyl-D-isoglutaminyl-2-(1',2'-O-dihexadecyl-sn-glycero-3'-hydroxyphosphoryloxy)ethylamide is obtained analogously to the manner described in Example 1 using 2-(1',2'-O-dihexadecyl-sn-glycero-3'-hydroxyphosphoryloxy)ethylamine and N-acetyldemethylmuramyl-L-alanyl-D-isoglutamine-N-hydroxysuccinimide ester as starting materials. $R_f$ value in a thin layer chromatogram over silica gel: 0.43 (in chloroform/methanol/water, 65:25:4).

The 2-(1',2'-O-dihexadecyl-sn-glycero-3'-hydroxyphosphoryloxy)ethylamine used as starting material is a commercially available synthetic preparation.

EXAMPLE 6

N-acetyldemethylmuramyl-L-alanyl-D-isoglutaminyl-2-(3'-O-palmitoyl-rac-glycero-1'-hydroxyphosphoryloxy)ethylamide is obtained analogously to the manner described in Example 1 using 2-(3'-O-palmitoyl-rac-glycero-1'-hydroxyphosphoryloxy)ethylamine and N-acetyldemethylmuramyl-L-alanyl-D-isoglutamine-N-hydroxysuccinimide ester as starting materials. $R_f$ value in a thin layer chromatogram over silica gel: 0.47 (in chloroform/methanol/water, 65:25:4).

The 2-(3'-O-palmitoyl-rac-glycero-1'-hydroxyphosphoryloxy)ethylamine used as starting material is a commercially available synthetic preparation.

EXAMPLE 7

N-acetyldemethylmuramyl-L-alanyl-D-isoglutaminyl-2-(1'-palmitoyl-2'-oleoyl-sn-glycero-3'-hydroxyphosphoryloxy)ethylamide is obtained analogously to the manner described in Example 1 using 2-(1'-O-palmitoyl-2'-O-oleoyl-sn-glycero-3'-hydroxyphosphoryloxy)ethylamine and N-acetyldemethylmuramyl-L-alanyl-D-isoglutamine-N-hydroxysuccinimide ester as starting materials. $R_f$ value in a thin layer chromatogram over silica gel: 0.33 (in chloroform/methanol/water, 65:25:4).

The 2-(1'-O-palmitoyl-2-O-oleoyl-sn-glycero-3'-hydroxyphosphoryloxy)ethylamine used as starting material is a commercially available synthetic preparation.

EXAMPLE 8

N-acetyldemethylmuramyl-L-alanyl-D-isoglutaminyl-2-(1'-palmitoyloxy-propyl-3'-oxyhydroxyphosphoryloxy)-ethylamide is obtained analogously to the manner described in Example 1 using 2-(1'-palmitoyloxy-propyl-3'-oxyhydroxyphosphoryloxy)ethylamine and N-acetyldemethylmuramyl-L-alanyl-D-isoglutamine-N-hydroxysuccinimide ester as starting materials.

$R_f$ value in a thin layer chromatogram over silica gel: 0.49 (in chloroform/methanol/water, 65:25:4).

The 2-(1'-palmitoyloxy-propyl-3'-oxyhydroxyphosphoryloxy)ethylamine used as starting material is a commercially available synthetic preparation.

EXAMPLE 9

N-acetylmuramyl-L-alanyl-D-isoglutaminyl-glycerophospholipid derivatives are obtained analogously to the manner described in the above Examples by condensing N-acetylmuramyl-L-alanyl-D-isoglutamine with the following phospholipids:

2-(1',2'-O-hexadecylidene-sn-glycero-3'-hydroxyphosphoryloxy)ethylamine,
2-(1'-O-palmitoyl-2'-O-oleoyl-sn-glycero-3'-hydroxyphosphoryloxy)ethylamine,
2-(3'-O-palmitoyl-rac-glycero-1'-hydroxyphosphoryloxy)ethylamine,
2-(1'-palmitoyloxy-propyl-3'-oxyhydroxyphosphoryloxy)-ethylamine.

EXAMPLE 10

N-acetylmuramyl-L-alanyl-D-isoglutaminyl-L-alanyl-glycerophospholipid derivatives are obtained analogously to the manner described in the above Examples by condensing N-acetylmuramyl-L-alanyl-D-isoglutaminyl-L-alanine with the following phospholipids:

2-(1',2'-O-hexadecylidene-sn-glycero-3'-hydroxyphosphoryloxy)ethylamine,
2-(1'-O-palmitoyl-2'-O-oleoyl-sn-glycero-3'-hydroxyphosphoryloxy)ethylamine,
2-(3'-O-palmitoyl-rac-glycero-1'-hydroxyphosphoryloxy)ethylamine,
2-(1'-palmitoyloxy-propyl-3'-oxyhydroxyphosphoryloxy)ethylamine.

EXAMPLE 11

N-acetyldemethylmuramyl-L-alanyl-D-isoglutaminyl-L-alanyl-glycerophospholipid derivatives are obtained analogously to the manner described in the above Examples by condensing N-acetylmuramyl-L-alanyl-D-isoglutaminyl-L-alanine with the following phospholipids:

2-(1',2'-O-dipalmitoyl-sn-glycero-3'-hydroxyphosphoryloxy)ethylamine,
2-(1',2'-O-hexadecylidene-sn-glycero-3'-hydroxyphosphoryloxy)ethylamine,
2-(1'-O-palmitoyl-2'-O-oleoyl-sn-glycero-3'-hydroxyphosphoryloxy)ethylamine,
2-(3'-O-palmitoyl-rac-glycero-1'-hydroxyphosphoryloxy)ethylamine,
2-(1'-palmitoyloxy-propyl-3'-oxyhydroxyphosphoryloxy)ethylamine.

The starting materials may be obtained as follows:

(A) 1.87 ml (11 mmol) of N,N-diisopropylethylamine, dissolved in 50 ml of dimethylformamide, are added dropwise in the course of ¼ hours to a solution of 6 g (10 mmol) of α-benzyl-N-acetylmuramyl-L-alanyl-D-isoglutamine and 1.75 ml (11 mmol) of bromoacetic acid benzyl ester in 100 ml of dimethylformamide while stirring well and with the exclusion of moisture. After stirring overnight at room temperature, the dimethylformamide is removed from the reaction mixture in a high vacuum and 100 ml of water are added to the residue. The precipitated oil quickly solidifies and crystallises completely. After stirring in the ice bath, the suspension is suction-filtered and the resulting crystals are washed with a little water and dried over phosphorus pentoxide.

After resuspending the crystals in petroleum ether, filtering and drying (50°), 6.2 g (85% of the theoretical yield) of colourless crystals remain; melting point 194; 195°-198° $[\alpha]_D^{20} + 1°$ (C=1,3; methanol).

(B) 6.5 g (8.85 mmol) of α-benzyl-N-acetylmuramyl-L-alanyl-D-isoglutamine-γ-benzyloxycarbonylmethyl ester are treated in 200 ml of methanol/water 1:1 in the presence of 0.5 g of 10% Pd on carbon for 40 hours (40°) with hydrogen.

The reaction mixture is freed of catalyst in the usual manner and the filtrate is evaporated to dryness.

The resulting oil is dissolved in 75 ml of water saturated with sec.-butanol, extracted 6 times with 50 ml each time of sec.-butanol saturated with water and once with ethyl acetate. The organic phases are reextracted with water (see above) and the combined aqueous phase are evaporated to dryness after treating with carbon (Darco G 60). The residue is twice mixed with water, evaporated and finally lyophilised.

4.0 g (82% of the theoretical yield) of white lyophilisate $[\alpha]_D^{20} + 34 \pm 1°$ are obtained (C=0.8; water).

(C) 6.1 g of α-benzyl-N-acetylmuramyl-L-alanyl-D-isoglutamien and 3.5 g of L-alaninebenzyl ester hydrochloride are dissolved in 30 ml of dimethylformamide, the solution is cooled to 0° and 1.4 ml of triethylamine, 1.1 g of N-hydroxysuccinimide and finally 2.3 g of dicyclohexylcarbodiimide are added in succession.

After stirring for 48 hours at room temperature the suspension is filtered, the precipitate is washed with a little dimethylformamide and the filtrate is evaporated to dryness in a high vacuum. The residue is suspended in 100 ml of water at 0° and the precipitate is filtered off and, after drying, recrystallised from methanol/water.

5.5 g (74% of the theoretical yield) are obtained; $[\alpha]_D^{20} + 70 + 1°$ (C=0.5; methanol).

(D) 3.4 g of α-benzyl-N-acetylmuramyl-L-alanyl-D-isoglutaminyl-L-alaninebenzyl ester, dissolved in 100 ml of methanol/water 2:1, are treated in the presence of 10% Pd on carbon for 40 hours with hydrogen. The catalyst is drawn off by suction, the filtrate is evaporated almost to dryness and the residue, after dissolving in 40 ml of water saturated with sec.-butanol, is extracted 3 times with 40 ml each time of sec. butanol saturated with water. After re-extraction of the organic phase with water (3×40 ml, see above), the combined aqueous extracts are evaporated and lyophilised. 2.2 g (80% of the theoretical yield) of colourless powder are obtained: $[\alpha]_D^{20} + 9 \pm 1°$ (C=1.1; water).

EXAMPLE 12

The following compounds are obtained in an analogous manner (determination of the analytical values as in Example 1):

N-benzoylmuramyl-L-alanyl-D-isoglutaminyl-2-(1',2'-O-dipalmitoyl-sn-glycero-3'-hydroxyphosphoryloxy)ethylamine.
N-benzoylmuramyl-L-alanyl-D-isoglutaminyl-2-(1'-O-palmitoyl-sn-glycero-3'-hydroxyphosphoryloxy)ethylamide,
N-benzoylmuramyl-L-alanyl-D-isoglutaminyl-2-(1'-palmitoyloxy-propyl-3'-oxyhydroxyphosphoryloxy)ethylamide,
N-benzoylmuramyl-L-alanyl-D-isoglutaminyl-2-(1',2'-O-dihexadecyl-rac-glycero-3'-hydroxyphosphoryloxy)ethylamide,
N-benzoylmuramyl-L-alanyl-D-isoglutaminyl-2-(1'-O-hexadecyl-rac-glycero-3'-hydroxyphosphoryloxy)ethylamide,
N-benzoylmuramyl-L-alanyl-D-isoglutaminyl-2-(1',3'-O-dipalmitoyl-glycero-2'-hydroxyphosphoryl)ethylamide,
N-benzoylmuramyl-L-alanyl-D-isoglutaminyl-L-alanyl-2-(1', 2'-O-dipalmitoyl-sn-glycero-3'-hydroxyphosphoryloxy)ethylamide, N-benzoylmuramyl-L-alanyl-D-isoglutaminyl-L-alanyl-2-(1'-O-palmitoyl-sn-glycero-3'-hydroxyphosphoryloxy)ethylamide, N-benzoylmuramyl-L-alanyl-D-isoglutaminyl-L-alanyl-2-(1'-palmitoyloxy-propyl-3'-oxyhydroxyphosphoryloxy)ethylamide, N-benzoylmuramyl-L-alanyl-D-isoglutaminyl-L-alanyl-2-(1',2'-O-dihexadexyl-rac-glycero-3'-hydroxyphosphoryloxy)ethylamide, N-benzoylmuramyl-L-alanyl-D-isoglutaminyl-L-alanyl-2-(1'-O-hexadecyl-rac-glycero-3'-hydroxyphosphoryloxy)ethylamide, N-benzoylmuramyl-L-alanyl-D-isoglutaminyl-L-alanyl-2-(1',3'-O-dipalmitoyl-glycero-2'-hydroxyphosphoryloxy)ethylamide, N-benzoylmuramyl-L-alanyl-D-glutaminyl-L-alanyl-2-(1',2'-O-dipalmitoyl-sn-glycero-3'-hydroxyphosphoryloxy)ethylamide, N-benzoylmuramyl-L-alanyl-D-glutaminyl-L-alanyl-2-(1'-O-palmitoyl-sn-glycero-3'-hydroxyphosphoryloxy)ethylamide, N-benzoylmuramyl-L-alanyl-D-glutaminyl-L-alanyl-2-(1'-palmitoyloxy-propyl-3'-oxyhydroxyphosphoryloxy)ethylamide, N-benzoylmuramyl-L-alanyl-D-glutaminyl-L-alanyl-2-(1',2'-O-dihexadecyl-rac-glycero-3'-hydroxyphosphoryloxy)ethylamide, N-benzoylmuramyl-L-alanyl-D-glutaminyl-L-alanyl-2-(1'-O-hexadecyl-rac-glycero-3'-hydroxyphosphoryloxy)ethylamide, N-benzoylmuramyl-L-alanyl-D-glutaminyl-L-alanyl-2-(1',3'-O-dipalmitoyl-glycero-2'-hydroxyphosphoryloxy)ethylamide, N-acetyldemethylmuramyl-L-seryl-D-isoglutaminyl-2-(1',2'-O-dipalmitoyl-sn-glycero-3'-hydroxyphosphoryloxy)ethylamide, N-acetyldemethylmuramyl-L-seryl-D-isoglutaminyl-2-(1'-O-palmitoyl-sn-glycero-3'-hydroxyphosphoryloxy)ethylamide, N-acetyldemethylmuramyl-L-seryl-D-isoglutaminyl-2-(1'-palmitoyloxy-propyl-3'-oxyhydroxyphosphoryloxy)ethylamide, N-acetyldemethylmuramyl-L-seryl-D-isoglutaminyl-2-(1',2'-O-dihexadexyl-rac-glycero-3'-hydroxyphosphoryloxy)ethylamide, N-acetyldemethylmuramyl-L-seryl-D-isoglutaminyl-2-(1'-O-hexadecyl-rac-glycero-3'-hydroxyphosphoryloxy)ethylamide, N-acetyldemethylmuramyl-L-seryl-D-isoglutaminyl-2-(1',3'-O-dipalmitoyl-glycero-2'-hydroxyphosphoryloxy)ethylamide, N-acetyldemethylmuramyl-L-seryl-D-isoglutaminyl-L-alanyl-2-(1',2'-O-dipalmitoyl-sn-glycero-3'-hydroxyphosphoryloxy)ethylamide, N-acetyl-demethylmuramyl-L-seryl-D-isoglutaminyl-L-alanyl-2-(1'-O-palmitoyl-sn-glycero-3'-hydroxyphosphoryloxy)ethylamide, N-acetyldemethylmuramyl-L-seryl-D-isoglutaminyl-L-alanyl-2-(1'-palmitoyloxy-propyl-3'-oxyhydroxyphosphoryloxy)ethylamide, N-acetyldemethylmuramyl-L-seryl-D-isoglutaminyl-L-alanyl-2-(1',2'-O-dihexadecyl-rac-glycero-3'-hydroxyphosphoryloxy)ethylamide, N-acetyldemethylmuramyl-L-seryl-D-isoglutaminyl-L-alanyl-2-(1'-O-hexadecyl-rac-glycero-3'-hydroxyphosphoryloxy)ethylamide, N-acetyldemethylmuramyl-L-seryl-D-isoglutaminyl-L-alanyl-2-(1',3'-O-dipalmitoyl-glycero-2'-hydroxyphosphoryloxy)ethylamide, N-acetyldemethylmuramyl-L-seryl-D-glutaminyl-L-alanyl-2-(1',2'-O-dipalmitoyl-sn-glycero-3'-hydroxyphosphoryloxy)ethylamide, N-acetyldemethylmuramyl-L-seryl-D-glutaminyl-L-alanyl-2-(1'-O-palmitoyl-sn-glycero-3'-hydroxyphosphoryloxy)ethylamide, N-acetyldemethylmuramyl-L-seryl-D-glutaminyl-L-alanyl-2-(1'-palmitoyloxy-propyl-3'-oxyhydroxyphosphoryloxy)ethylamide, N-acetyldemethylmuramyl-L-seryl-D-glutaminyl-L-alanyl-2-(1',2'-O-dihexadexyl-rac-glycero-3'-hydroxyphosphoryloxy)ethylamide, N-acetyldemethylmuramyl-L-seryl-D-lgutaminyl-L-alanyl-2-(1'-O-hexadecyl-rac-glycero-3'-hydroxyphosphoryloxy)ethylamide, N-acetyldemethylmuramyl-L-seryl-D-glutaminyl-L-alanyl-2-(1',3'-O-dipalmitoyl-glycero-2'-hydroxyphosphoryloxy)ethylamide, N-acetyldemethylmuramyl-L-aminobutyryl-D-isoglutaminyl-2-(1',2'-O-dipalmitoyl-sn-glycero-3'-hydroxyphosphoryloxy) ethylamide, N-acetyldemethylmuramyl-L-α-aminobutyryl-D-isoglutaminyl-2-(1'-O-palmitoyl-sn-glycero-3'-hydroxyphosphoryloxy)ethylamide, N-acetyldemethylmuramyl-L-α-aminobutyryl-D-isoglutaminyl-2-(1'-palmitoyloxy-propyl-3'-oxyhydroxyphosphoryloxy)ethylamide, N-acetyldemethylmuramyl-L-α-aminobutyryl-D-isoglutaminyl-2-(1',2'-O-dihexadecyl-rac-glycero-3'-hydroxyphosphoryloxy)ethylamide, N-acetyldemethylmuramyl-L-α-aminobutyryl-D-isoglutaminyl-2-(1'-O-hexadecyl-rac-glycero-3'-hydroxyphosphoryloxy)ethylamide, N-acetyldemethylmuramyl-L-α-aminobutyryl-D-isoglutaminyl-2-(1',3'-O-dipalmitoyl-glycero-2'-hydroxyphosphoryl)ethylamide, N-acetyldemethylmuramyl-L-α-aminobutyryl-D-isoglutaminyl-L-alanyl-2-(1',2'-O-dipalmitoyl-sn-glycero-3'-hydroxyphosphoryloxy)ethylamide, N-acetyldemethylmuramyl-L-α-aminobutyryl-D-isoglutaminyl-L-alanyl-2-(1'-O-palmitoyl-sn-glycero-3'-hydroxyphosphoryloxy)ethylamide, N-acetyldemethylmuramyl-L-α-aminobutyryl-D-isoglutaminyl-L-alanyl-2-(1'-palmitoyloxy-propyl-3'-oxyhydroxyphosphoryloxy)-ethylamide, N-acetyldemethylmuramyl-L-α-aminobutyryl-D-isoglutaminyl-L-alanyl-2-(1',2'-O-dihexadecyl-rac-glycero-3'-hydroxyphosphoryloxy)ethylamide, N-acetyldemethylmuramyl-L-α-aminobutyryl-D-isoglutaminyl-L-alanyl-2-(1'-O-hexadecyl-rac-glycero-3'-hydroxyphosphoryloxy)ethylamide, N-acetyldemethylmuramyl-L-α-aminobutyryl-D-isoglutaminyl-L-alanyl-2-(1',3'-O-dipalmitoyl-glycero-2'-hydroxyphosphoryloxy)ethylamide, N-acetyldemethylmuramyl-L-α-aminobutyryl-D-glutaminyl-L-alanyl-2-(1',2'-O-dipalmitoyl-sn-glycero-3'-hydroxyphosphoryloxy)ethylamide, N-acetyldemethylmuramyl-L-α-aminobutyryl-D-glutaminyl-L-alanyl-2-(1'-O-palmitoyl-sn-glycero-3'-hydroxyphosphoryloxy)ethylamide, N-acetyldemethylmuramyl-L-α-aminobutyryl-D-glutaminyl-L-alanyl-2-(1'-palmitoyloxy-propyl-3'-oxyhydroxyphosphoryloxy)ethylamide, N-acetyldemethylmuramyl-L-α-aminobutyryl-D-glutaminyl-L-alanyl-2-(1',2'-O-dihexadecyl-rac-glycero-3'-hydroxyphosphoryloxy)ethylamide, N-acetyldemethylmuramyl-L-α-aminobutyryl-D-glutaminyl-L-alanyl-2-(1'-O-hexadecyl-rac-glycero-3'-hydroxyphosphoryloxy)ethylamide, N-acetyldemethylmuramyl-L-2-aminobutyryl-D-glutaminyl-L-alanyl-2-(1',3'-O-dipalmitoyl-glycero-2'-hydroxyphosphoryloxy)ethylamide, N-acetylmuramyl-L-α-aminobutyryl-D-isoglutaminyl-2-(1',2'-O-dipalmitoyl-sn-glycero-3'-hydroxyphosphoryloxy)ethylamide, N-acetylmuramyl-L-α-aminobutyryl-D-isoglutaminyl-2-(1'0-palmitoyl-sn-glycero-3'-hydroxyphosphoryloxy)ethylamide, N-acetylmuramyl-L-α-aminobutyryl-D-isoglutaminyl-2-(1'-palmitoyloxy-propyl-3'-oxyhydroxyphosphoryloxy)ethylamide, N-acetylmuramyl-L-α-aminobutyryl-D-isoglutaminyl-2-(1',2'-O-dihexadecyl-rac-glycero-3'-hydroxyphosphoryloxy)ethylamide, N-acetylmuramyl-L-α-aminobutyryl-D-isoglutaminyl-2-(1'-O-hexadecyl-rac-glycero-3'-hydroxyphosphoryloxy)ethylamide, N-acetylmuramyl-L-α-aminobutyryl-D-isoglutaminyl-2-(1',3'-O-dipalmitoyl-glycero-2'-hydroxyphosphoryloxy)ethylamide, N-acetylmuramyl-L-α-aminobutyryl-D-isoglutaminyl-L-alanyl-2-(1',2'-O-dipalmitoyl-sn-glycero-3'-hydroxyphosphoryloxy)ethylamide, N-acetylmuramyl-L-α-aminobutyryl-D-isoglutaminyl-L-alanyl-2-(1'-O-palmitoyl-sn-glycero-3'-hydroxyphosphoryloxy)ethylamide, N-acetylmuramyl-L-α-aminobutyryl-D-isoglutaminyl-L-alanyl-2-(1'-palmitoyloxy-propyl-3'-oxyhydroxyphosphoryl)ethylamide, N-acetylmuramyl-L-α-aminobutyryl-D-isoglutaminyl-L-alanyl-2-(1',2'-O-dihexadecyl-rac-glycero-3'-hydroxyphosphoryloxy)ethylamide, N-acetylmuramyl-L-α-aminobutyryl-D-isoglutaminyl-L-alanyl-2-(1'-O-hexadecyl-rac-glycero-3'-hydroxyphosphoryloxy)ethylamide, N-acetylmuramyl-L-α-aminobutyryl-D-isoglutaminyl-L-alanyl-2-(1',3'-O-dipalmitoyl-glycero-2'-hydroxyphosphoryloxy)ethylamide, N-acetylmuramyl-L-α-aminobutyryl-D-glutaminyl-L-alanyl-2-(1',2'-O-dipalmitoyl-sn-glycero-3'-hydroxyphosphoryloxy)ethylamide, N-acetylmuramyl-L-α-aminobutyryl-D-glutaminyl-L-alanyl-2-(1'-O-palmitoyl-sn-glycero-3'-hydroxyphosphoryloxy)ethylamide, N-acetylmuramyl-L-α-aminobutyryl-D-glutaminyl-L-alanyl-2-(1'-palmitoyloxy-propyl-3'-oxyhydroxyphosphoryloxy)ethylamide, N-acetylmuramyl-L-α-aminobutyryl-D-glutaminyl-L-alanyl-2-(1',2'-O-dihexadecyl-rac-glycero-3'-hydroxyphosphoryloxy)ethylamide, N-acetylmuramyl-L-α-aminobutyryl-D-glutaminyl-L-alanyl-2-(1'-O-hexadecyl-rac-glycero-3'-hydroxyphosphoryloxy)ethylamide, N-acetylmuramyl-L-α-aminobutyryl-D-glutaminyl-L-alanyl-2-(1',3'-O-dipalmitoyl-glycero-2'-hydroxyphosphoryloxy)ethylamide, N-acetyldemethylmuramyl-L-alanyl-D-glutamyl-α-carbamoylmethylamino-γ-2-(1',2'-O-dipalmitoyl-sn-glycero-3'-hydroxyphosphoryloxy)ethylamide, N-acetyldemethylmuramyl-L-alanyl-D-glutamyl-α-carbamoylmethylamino-γ-L-alanyl-2-(1',2'-O-dipalmitoyl-sn-glycero-3'-hydroxyphosphoryloxy)ethylamide, N-acetyldemethylmuramyl-L-alanyl-D-glutaminyl-L-alanyl-2-(1',2'-O-dipalmitoyl-sn-glycero-3'-hydroxyphosphoryloxy)ethylamide, N-acetyldemethylmuramyl-L-alanyl-D-glutaminyl-2-(1',2'-O-dipalmitoyl-sn-glycero-3'-hydroxyphosphoryloxy)ethylamide, N-acetyldemethylmuramyl-L-seryl-D-glutaminyl-2-(1',2'-O-dipalmitoyl-sn-glycero-3'-hydroxyphosphoryloxy)ethylamide, N-acetyldemethylmuramyl-L-α-aminobutyryl-D-glutaminyl-2-(1',2'-O-dipalmitoyl-sn-glycero-3'-hydroxyphosphoryloxy)ethylamide, N-acetylmuramyl-L-α-aminobutyryl-D-glutaminyl-2-(1',2'-O-dipalmitoyl-sn-glycero-3'-hydroxyphosphoryloxy)ethylamide, N-acetylmuramyl-L-valyl-D-isoglutaminyl-2-(1',2'-O-dipalmitoyl-sn-glycero-3'-hydroxyphosphoryl)ethylamide, N-acetylmuramyl-L-valyl-D-isoglutaminyl-L-alanyl-2-(1',2'-O-dipalmitoyl-sn-glycero-3'-hydroxyphosphoryloxy)ethylamide, N-propionylnormuramyl-L-alanyl-D-isoglutaminyl-2-(1',2'-O-dipalmitoyl-sn-glycero-3'-hydroxyphosphoryloxy)ethylamide, N-propionylnormuramyl-L-alanyl-D-isoglutaminyl-L-alanyl-2-(1',2'-O-dipalmitoyl-sn-glycero-3'-hydroxyphosphoryloxy)ethylamide, N-acetylmuramyl-L-prolyl-D-isoglutaminyl-2-(1',2'-O-dipalmitoyl-sn-glycero-3'-hydroxyphosphoryloxy)ethylamide, N-acetylmuramyl-L-prolyl-D-isoglutaminyl-L-alanyl-2-(1',2'-O-dipalmitoyl-sn-glycero-3'-hydroxyphosphoryloxy)ethylamide, N-benzoylnurmuramyl-L-α-aminobutyryl-D-isoglutaminyl-2-(1',2'-O-dipalmitoyl-sn-glycero-3'-hydroxyphosphoryloxy)ethylamide, N-benzoylnormuramyl-L-α-aminobutyryl-D-isoglutaminyl-L-alanyl-2-(1',2'-O-dipalmitoyl-sn-glycero-3'-hydroxyphosphoryloxy)-ethylamide, N-acetylmuramyl-L-threonyl-D-isoglutaminyl-2-(1',2'-O-dipalmitoyl-sn-glycero-3-hydroxyphosphorylox-y)ethylamide, N-acetylmuramyl-L-threonyl-D-isoglutaminyl-L-alanyl-2-(1',2'-O-dipalmitoyl-sn-glycero-3'-hydroxyphosphoryloxy)ethylamide.

N-acetyldemethylmuramyl-L-alanyl-D-isoglutamine 2-(1'-O-hexadecyl-sn-glycero-3'-hydroxyphosphoryloxy)ethylamide.

N-acetylmuramyl-L-alpha-aminobutyryl-D-isoglutaminyl-L-alanine 2-(1',2'-O-dipalmitoyl-rac-glycero-3'-hydroxyphosphoryloxy)ethylamide.

N-benzoylmuramyl-L-alpha-aminobutyryl-D-isoglutaminyl-L-alanine 2-(1',2'-O-dipalmitoyl-sn-glycero-3'-hydroxyphosphoryloxy)ethylamide.

EXAMPLE 13

A solution of 1.5 mmol of N-acetylmuramyl-L-alanyl-D-isoglutaminyl-L-alanine-N-hydroxysuccinimide ester in 5 ml of dimethylacetamide is added dropwise to a solution of 1 mmol of 2-(1',2'-O-dipalmitoyl-sn-glycero-3'-hydroxyphosphoryloxy)ethylamide and 3.5 mmol of N-ethylmorpholine in 25 ml of chloroform-/methanol/water=65/25/4 at room temperature. After stirring 8 hours at room temperature (about 22°) the reaction is finished. 130 ml of water are added to the reaction mixture.

After having removed the organic solvents under reduced pressure the resulting aqueous solution which may still contain some methanol is filtered through a teflon millipore filter (5 μm). The stirred filtrate is dialysed in a Amicon ultrafiltration cell through a Amicon YM 10 membrane successively against 400 ml of water, 200 ml of an aqueous 0.1 molar sodium phosphate buffer/0.1 molar sodium chloride solution pH 7, and 850 ml of water in the diafiltration process. The inner dialysate is filtered through a Millipore filter (0.45 μm) and freeze-dried whereupon N-acetylmuramyl-L-alanyl-D-isogutaminyl-L-alanyl-2-(1',2'-O-dipalmitoyl-sn-glycero-3'-hydroxyphosphoryloxy)ethylamide is obtained which is mostly or totally present in the form of its sodium salt.

Analysis for product (calculated values for 100% sodium salt containing three moles of water per mole salt)

| $C_{59}H_{114}N_6O_{22}P$ Na (1315.55) | | | | | |
|---|---|---|---|---|---|
| Calc.: | C 53.59 | H 8.75 | N 6.40 | P 2.36 | Na 1.75 |
| Exp.: | C 53.89 | H 8.63 | N 6.40 | P 2.22 | Na 1.58 |

EXAMPLE 14

By the procedure described in example 13 the compounds of the formula I mentioned in the examples 1 to 3 and 5 to 12 are obtained mostly or totally in the form of the corresponding sodium salts.

EXAMPLE 15

Multilamellar vesicles (liposomes) are prepared from a mixture (molar ratio 7:3) of chromatographically pure egg phosphatidylcholine and beef brain phosphatidylserine (both purchased from Avanti Biochemicals, Birmingham, AL), mechanically agitated on a Vortex mixer, slighthly modified as described in G. Poste, R. Kirsh, W. Fogler and I. J. Fidler, Cancer Res. 39, 881–892 (1979) and references cited therein:

In order to prepare 1 ml of liposomes, 35 μmol egg phosphatidylcholine, 15 μmol beef brain phosphatidylserine and 100–200 μg N-acetyl-muramyl-L-alanyl-D-isoglutaminyl-L-alanyl-2-(1',2'-O-dipalmitoyl-sn-glycero-3'-hydroxyphosphoryloxy)-ethylamide are dissolved in 20 ml of chloroform in a 50 ml round flask. The solvent is evaporated by rotary evaporation under reduced pressure of nitrogen so that a uniform film of lipid is formed on the walls of the flask. The remaining solvent is then evaporated in a high vacuum. The obtained lipid film is shaken with 1 ml of phosphate buffered saline solution at 37°, whereupon multilamellar vesicles are formed, in the lipid bilayer of which the muramyl peptide is incorporated.

The pharmaceutical preparation thus obtained must be used (injected intravenously) within 4 hours.

We claim:

1. Muramyl peptides of the formula

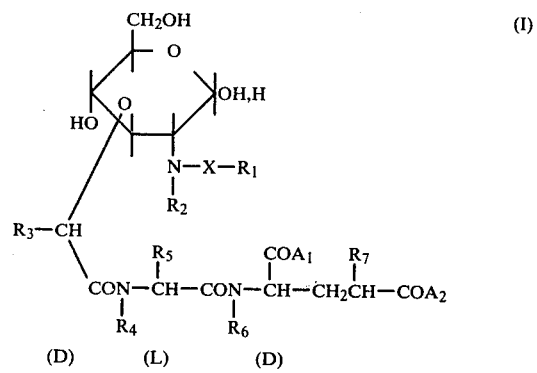

in which
X represents carbonyl or carbonyloxy,
$R_1$ represents optionally substituted alkyl or aryl,
$R_2$, $R_4$ and $R_6$ represent hydrogen or lower alkyl,
$R_3$ represents hydrogen or lower alkyl,
$R_5$ represents hydrogen, lower alkyl, free or functionally modified hydroxy-lower alkyl, free or functionally modified mercapto-lower alkyl, optionally substituted amino-lower alkyl, cycloalkyl, cycloalkyl-lower alkyl, optionally substituted aryl or aralkyl, or nitrogen-containing heterocyclyl or heterocyclyl-lower alkyl,
$R_4$ and $R_5$ together also represent alkylene having 3 or 4 carbon atoms,
$R_7$ represents hydrogen or optionally esterified or amidated carboxyl and
one of the radicals $A_1$ and $A_2$ represents a radical of the formula

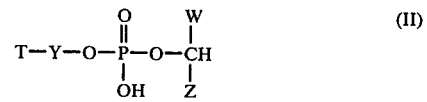

in which
T represents -NH or -O,
Y represents an optionally substituted alkylene group which may also be interrupted by one or two oxycarbonyl and/or iminocarbonyl groups,
W represents hydrogen, and
Z represents a 1,2-dihydroxyethyl or 2-hydroxyethyl group in which at least one of the hydroxy groups is esterified by an optionally unsaturated, long-chained aliphatic carboxylic acid or etherified by an optionally unsaturated, long-chained aliphatic alcohol, or W and Z each represents a hydroxymethyl group esterified by an optionally unsaturated, long-chained aliphatic carboxylic acid or etherified by an optionally unsaturated, long-chained aliphatic alcohol,
and the other of the radicals $A_1$ and $A_2$ is free or etherified hydroxy, amino, lower alkylamino or aminocarbonyl lower alkylamino, and pharmaceutically acceptable salts thereof.

2. Muramyl peptides according to claim 1, in which Y is a lower alkylene radical which preferably has 2 or 3 carbon atoms, and pharmaceutically acceptable salts thereof.

3. Muramyl peptides according to claim 1, in which Y represents a radical of the formula

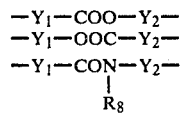

or

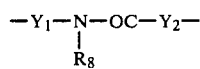

in which one of the radicals $Y_1$ and $Y_2$ represents an optionally substituted lower alkylene radical and the other represents an optionally substituted lower alkylene radical which may also be interrupted by oxycarbonyl or N-$R_8$-aminocarbonyl, and $Y_1$ and $Y_2$ together have more than two carbon atoms and $R_8$ represents hydrogen or lower alkyl, and pharmaceutically acceptable salts thereof.

4. Muramyl peptides of the formula I according to claim 1, in which X represents carbonyl, $R_5$ represents hydrogen; lower alkyl optionally substituted by hydroxy, lower alkoxy, mercapto, lower alkylthio or halogen; cycloalkyl or cycloalkyl-lower alkyl, wherein the cycloalkyl radical contains 4–6 carbon atoms; optionally substituted phenyl or phenyl-lower alkyl, heterocyclyl or heterocyclyl-lower alkyl containing one or two nitrogen atoms, or $R_4$ and $R_5$ together also represent alkylene having 3 or 4 carbon atoms, $R_7$ represents hydrogen, one of the radicals $A_1$ and $A_2$ represents a radical of the formula

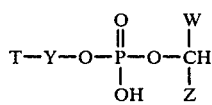

in which T represents -NH or -O and Y represents optionally substituted alkylene which may also be interrupted by oxycarbonyl or iminocarbonyl, and the other of the radicals $A_1$ and $A_2$ represents hydroxy, lower alkoxy, amino, lower alkylamino or aminocarbonyl-lower alkylamino, and pharmaceutically acceptable salts thereof.

5. Muramyl peptides of the formula I according to claim 1, in which X represents carbonyl, $R_1$ represents lower alkyl which is unsubstituted or substituted by hydroxy, lower alkoxy or halogen, or phenyl which is unsubstituted or substituted by hydroxy, lower alkoxy, lower alkyl or halogen, $R_2$, $R_4$ and $R_6$ represent hydrogen, $R_5$ represents hydrogen, lower alkyl having 1–3 carbon atoms which is unsubstituted or substituted by hydroxy, lower alkoxy, mercapto, lower alkylthio or halogen; cycloalkyl or cycloalkyl-lower alkyl in which the cycloalkyl radical contains 4–6 carbon atoms and the lower alkyl radical contains 1–3 carbon atoms; phenyl or phenyl-lower alkyl having 1–3 carbon atoms in the lower alkyl radical both unsubstituted or substituted by hydroxy, lower alkoxy or halogen; or heterocyclyl or heterocyclyl-lower alkyl having 1–3 carbon atoms in the lower alkyl radical and each containing 5 or 6 ring members and one or two nitrogen atoms, or $R_4$ and $R_5$ together represent also alkylene with 3 or 4 carbon atoms, $R_7$ represents hydrogen, and one of the radicals $A_1$ and $A_2$ represents a radical of the formula

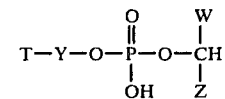

in which T represents -NH or -O, Y represents optionally substituted lower alkylene or a radical of the formula

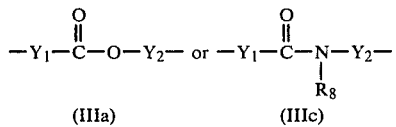

in which $R_8$ represents hydrogen and $Y_1$ and $Y_2$ each represents optionally substituted lower alkylene, W represents hydrogen and Z represents a 1,2-dihydroxyethyl or 2-hydroxyethyl group in which at least one of the hydroxy groups is esterified by a saturated or singly or doubly unsaturated aliphatic carboxylic acid having 16–22 carbon atoms or by a natural or synthetic mycolic acid, or is etherified by a saturated or singly or doubly unsaturated, aliphatic alcohol having 12–18 carbon atoms, and the other or the radicals $A_1$ and $A_2$ represents hydroxy, lower alkoxy, amino, lower alkylamino or aminocarbonyl-lower alkylamino, and pharmaceutically acceptable salts thereof.

6. Muramyl peptides of the formula I according to claim 1, in which X represents carbonyl, $R_1$ represents lower alkyl having 1–3 carbon atoms or phenyl, $R_2$, $R_4$ and $R_6$ represent hydrogen, $R_3$ represents hydrogen or lower alkyl having 1–3 carbon atoms, $R_5$ represents hydrogen, lower alkyl having 1–3 carbon atoms which is unsubstituted or substituted by hydroxy, methoxy, mercapto, methylthio or halogen; phenyl or phenylmethyl each unsubstituted or substituted by hydroxy, methoxy or halogen; or heterocyclyl or heterocyclylmethyl each containing one or two nitrogen atoms and having 5 ring members, or $R_4$ and $R_5$ together also represent trimethylene, $R_7$ represents hydrogen and one of the radicals $A_1$ and $A_2$ represents a radical of the formula

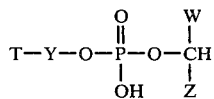

in which T represents -NH or -O, Y represents lower alkylene having 2 or 3 carbon atoms or a radical of the formula (IIIa) or (IIIc)

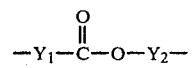

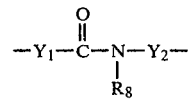

in which $R_8$ represents hydrogen and $Y_1$ and $Y_2$ independently of one another each represents lower alkylene having 1–3 carbon atoms which is unsubstituted or substituted by hydroxy, lower alkoxy, mercapto, lower alkylthio, by optionally hydroxy-, methoxy- or halogen-substituted phenyl or phenyl-lower alkyl, or by heterocyclyl or heterocyclyl-lower alkyl having 1–3 carbon atoms in the lower alkyl radical and each containing 5 or 6 ring members and one or two nitrogen atoms, W represents hydrogen and Z represents a 1,2-dihydroxyethyl or 2-hydroxyethyl group in which at least one of the hydroxy groups is esterified with a saturated or singly or doubly unsaturated aliphatic carboxylic acid having 16 to 20 carbon atoms or etherified with a saturated or singly or doubly unsaturated aliphatic alcohol having 12–18 carbon atoms, and the other of the radicals $A_1$ and $A_2$ represents hydroxy, lower alkoxy, amino, lower alkylamino or aminocarbonyl-lower alkylamino, and pharmaceutically acceptable salts thereof.

7. Muramyl peptides of the formula I according to claim 1, wherein X represents carbonyl, $R_1$ represents lower alkyl which is unsubstituted or substituted by hydroxy, lower alkoxy or by halogen; or phenyl which is unsubstituted or substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms which is unsubstituted or substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical which are substituted or substituted in the phenyl-moiety by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

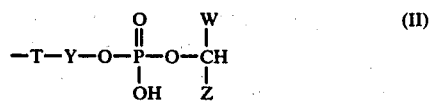

wherein T represents -NH or -O, Y represents optionally substituted lower alkylene or a radical of the formula

or

in which $R_8$ represents hydrogen or methyl and each of $Y_1$ and $Y_2$ independently of the other represents lower alkylene that has from 1 to 7 carbon atoms and is unsubstituted or substituted by hydroxy, lower alkoxy, mercapto, methylthio, phenyl, 4-imidazolyl or by 3-indolyl, W represents hydrogen and Z represents a 1,2-dihydroxyethyl or 2-hydroxyethyl group in which at least one hydroxy group is esterified by an aliphatic carboxylic acid having from 12 to 24 carbon atoms which is saturated or contains one or two double bonds, or by a natural or synthetic mycolic acid or etherified by an aliphatic alcohol having from 10 to 22 carbon atoms which is saturated or contains one or two double bonds, or each of W and Z represents a hydroxymethyl group esterified by an aliphatic carboxylic acid having from 12 to 24 carbon atoms which is saturated or contains one or two double bonds, or by a natural or synthetic mycolic acid or etherified by an aliphatic alcohol having from 10 to 22 carbon atoms which is saturated or contains one or two double bonds, and the other of the radicals $A_1$ and $A_2$ is hydroxy, lower alkoxy, amino, lower alkylamino or aminocarbonyl-lower alkylamino and pharmaceutically acceptable salts thereof.

8. Muramyl peptides of the formula I according to claim 1, in which $R_1$ represents lower alkyl having 1 to 3 carbon atoms or phenyl, $R_2$, $R_4$ and $R_6$ represent hydrogen, $R_3$ represents hydrogen or lower alkyl having 1 to 3 carbon atoms, $R_5$ represents hydrogen or lower alkyl, $R_7$ represents hydrogen, $A_1$ represents amino, lower alkylamino, hydroxy or lower alkoxy and $A_2$ represents a radical of the formula (II) according to claim 1, in which T represents -NH or -O, Y represents lower alkylene having 2 or 3 carbon atoms or a radical of the formula $CH_2$-$CO$-$NH$-$CH_2$-$CH_2$, W represents hydrogen and Z represents a 1,2-dihydroxyethyl group or 2-hydroxy-ethyl group in which one or two hydroxy groups are esterified by identical or different saturated or singly or doubly unsaturated alkane carboxylic acids having 16 to 22 carbon atoms or etherified by a saturated or singly or doubly unsaturated alkanol having 12 to 18 carbon atoms, or in which W and Z each represent a hydroxymethyl group which is esterified by a saturated or singly or doubly unsaturated alkane carboxylic acid having 16 to 22 carbon atoms or etherified by a saturated or singly or doubly unsaturated alkanol having 12 to 18 carbon atoms, and pharmaceutically acceptable salts thereof.

9. Muramyl peptides of the formula I according to claim 1, wherein X represents carbonyl, $R_1$ represents lower alkyl or phenyl, $R_2$, $R_6$ and $R_7$ represent hydrogen, $R_3$ and $R_4$ represent hydrogen or methyl, $R_5$ represents lower alkyl having from 1 to 4 carbon atoms, $A_1$ represents amino and $A_2$ represents a radical of the formula

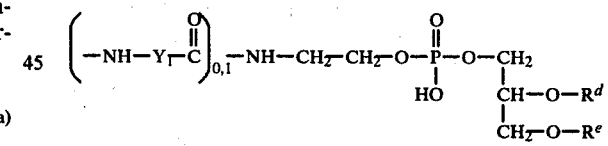

wherein $Y_1$ represents a radical of one of the formulae

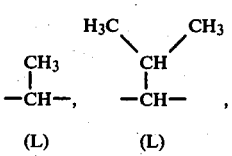

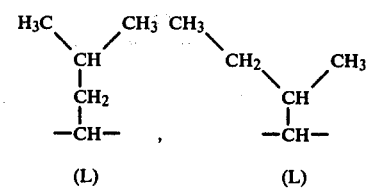

and $R^d$ and $R^e$ independently of one another represent the acyl radical of an unsubstituted aliphatic carboxylic acid having from 12 to 22 carbon atoms, which is saturated or contains one or two double bonds, and the pharmaceutically acceptable salts thereof.

10. Muramyl peptides of the formula I according to claim 1 in which
X represents carbonyl,
$R_1$ represents methyl, ethyl or phenyl,
$R_2$, $R_6$ and $R_7$ represent hydrogen,
$R_3$ and $R_4$ represent hydrogen or methyl,
$R_5$ represents methyl or ethyl,
$A_1$ represents amino and
$A_2$ represents a radical of the formula

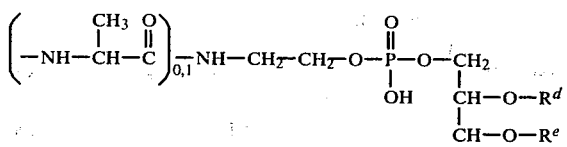

wherein $R^d$ and $R^e$ independently of one another represent the acyl radical of an unsubstituted and unbranched aliphatic carboxylic acid having from 12 to 22 carbon atoms, which is saturated or contains one or two double bonds, and the pharmaceutically acceptable salts thereof.

11. Compounds according to any one of claims 8 to 10, in which the meanings of $A_1$ and $A_2$ are reversed, and pharmaceutically acceptable salts thereof.

12. Compounds according to any one of claims 1 to 10 in which $R_1$ represents lower alkyl.

13. A compound according to claim 1 which is N-acetylmuramyl-L-alanyl-D-isoglutamine 2-(1',2'-O-dipalmitoyl-sn-glycero-3'-hydroxyphosphoryloxy)ethylamide and pharmaceutically acceptable salts thereof.

14. A compound according to claim 1 which is N-acetyldemethylmuramyl-L-alanyl-D-isoglutamine 2-(1',2'-O-dipalmitoyl-sn-glycero-3'-hydroxyphosphoryloxy)ethylamide and pharmaceutically acceptable salts thereof.

15. A compound according to claim 1 which is N-acetylmuramyl-L-alanyl-D-isoglutaminyl-oxy-methylcarboxylic acid 2-(1',2'-O-dipalmitoyl-sn-glycero-3'-hydroxyphosphoryloxy)ethylamide and pharmaceutically acceptable salts thereof.

16. A compound according to claim 1 which is N-acetyldemethylmuramyl-L-alanyl-D-isoglutamine 2-(1',2'-O-dihexadecyl-sn-glycero-3'-hydroxyphosphoryloxy)ethylamide and pharmaceutically acceptable salts thereof.

17. A compound according to claim 1 which is N-acetyldemethylmuramyl-L-alanyl-D-isoglutamine 2-(1'-O-hexadecyl-sn-glycero-3'-hydroxyphosphoryloxy)ethylamide and pharmaceutically acceptable salts thereof.

18. A compound according to claim 1 which is N-acetyldemethylmuramyl-L-alanyl-D-isoglutamine 2-(3'-O-palmitoyl-rac-glycero-1'-hydroxyphosphoryloxy)ethylamide and pharmaceutically acceptable salts thereof.

19. A compound according to claim 1 which is N-acetyldemethylmuramyl-L-alanyl-D-isoglutamine 2-(1'-O-palmitoyl-2'-O-oleoyl-sn-glycero-3'-hydroxyphosphoryloxy)ethylamide and pharmaceutically acceptable salts thereof.

20. A compound according to claim 1 which is N-acetyldemethylmuramyl-L-alanyl-D-isoglutamine 2-(1'-palmitoyloxypropyl-3'-oxyhydroxyphosphoryloxy)ethylamide and pharmaceutically acceptable salts thereof.

21. A compound according to claim 1 which is n-acetylmuramyl-L-α-aminobutyryl-D-isoglutaminyl-L-alanine 2-(1',2'-O-dipalmitoyl-sn-glycero-3'-hydroxyphosphoryloxy)ethylamide and pharmaceutically acceptable salts thereof.

22. A compound according to claim 1 which is N-acetylmuramyl-L-α-aminobutyryl-D-isoglutaminyl-L-alanine 2-(1',2'-O-dipalmitoyl-rac-glycero-3'-hydroxyphoshoryloxy)ethylamide and pharmaceutically acceptable salts thereof.

23. A compound according to claim 1 which is N-benzoylmuramyl-L-α-aminobutyryl-D-isoglutaminyl-L-alanine 2-(1',2'-O-dipalmitoyl-sn-glycero-3'-hydroxyphosphoryloxy)ethylamide and pharmaceutically acceptable salts thereof.

24. A compound according to claim 1 which is N-propionyldemethylmuramyl-L-alanyl-D-isoglutaminyl-L-alanine 2-(1',2'-O-dipalmitoyl-sn-glycero-3'-hydroxyphosphoryloxy)ethylamide and pharmaceutically acceptable salts thereof.

25. A compound according to claim 1 which is N-acetylmuramyl-L-valyl-D-isoglutaminyl-L-alanine 2-(1',2'-O-dipalmitoyl-sn-glycero-3'-hydroxyphosphoryloxy)ethylamide and pharmaceutically acceptable salts thereof.

26. A compound according to claim 1 which is N-benzoyldemethylmuramyl-L-α-aminobutyryl-D-isoglutaminyl-L-alanine 2-(1',2'-O-dipalmitoyl-sn-glycero-3'-hydroxyphosphoryloxy)ethylamide and pharmaceutically acceptable salts thereof.

27. A compound according to claim 1 which is N-acetyldemethylmuramyl-L-alanyl-D-glutamyl-α-carbamoylmethylamino-γ-L-alanine 2-(1',2'-O-dipalmitoyl-sn-glycero-3'-hydroxyphosphoryloxy)ethylamide and pharmaceutically acceptable salts thereof.

28. N-acetylmuramyl-L-alanyl-D-isogutaminyl-L-alanine 2-(1',2'-O-dipalmitoyl-sn-glycero-3'-hydroxyphosphoryloxy)ethylamide and pharmaceutically acceptable salts thereof.

29. A compound according to claim 28 which is the sodium salt.

30. A pharmaceutical composition useful for modulating the immune response of warm-blooded animals including man which comprises as active ingredient an effective dose of a pharmaceutically acceptable salt of a muramyl peptide according to claim 1, or a mixture of such a muramyl peptide and such a salt in association with a significant amount of a pharmaceutically acceptable carrier.

31. A pharmaceutical composition as claimed in claim 30 for parenteral administration and for potentiating the immune response of man which contains 0,01 mg to 0.5 mg of the active ingredient per dosage unit in association with liposomes as a carrier.

32. Method for modulating the immune system of warm-blooded animals including man which comprises administering parenterally an effective dose of a pharmaceutically acceptable salt of a muramyl peptide according to claim 1, or a mixture of a muramyl peptide and such a salt.

33. Method for stimulating the immune system of a human patient which comprises administering at the same time intravenously 0,01 to 0,5 mg per day of a pharmaceutically acceptable salt of a muramyl peptide according to claim 1, or a mixture of a muramyl peptide and such a salt in association with liposomes as a carrier.

34. Compounds of formula I according to any one of claims 8-10 in which the meanings of $A_1$ and $A_2$ are reversed and in which $R_1$ represents a lower alkyl residue, and pharmaceutically acceptable salts thereof.

35. Muramyl peptides according to claim 7 wherein the salts are metal salts or ammonium salts from ammonia or organic amines.

36. Muramyl peptides according to claim 8 wherein the salts are metal salts or ammonium salts from ammonia or organic amines.

37. Muramyl peptides according to claim 9 wherein the salts are metal salts or ammonium salts from ammonia or organic amines.

38. Muramyl peptides according to claim 10 wherein the salts are metal salts or ammonium salts from ammonia or organic amines.

39. Muramyl peptides according to claim 11 wherein the salts are metal salts or ammonium salts from ammonia or organic amines.

40. Muramyl peptides according to claim 12 wherein the salts are metal salts or ammonium salts from ammonia or organic amines.

41. Muramyl peptides according to claim 15 wherein the salts are metal salts or ammonium salts from ammonia or organic amines.

42. Muramyl peptides according to claim 28 wherein the salts are metal salts or ammonium salts from ammonia or organic amines.

43. A pharmaceutical composition useful for modulating the immune response of warm-blooded animals including man which comprises as active ingredient an effective dose of a pharmaceutically acceptable salt of a muramyl peptide according to claim 28, or a mixture of such a muramyl peptide and such a salt in association with a significant amount of a pharmaceutically acceptable carrier.

* * * * *